US012646165B2

(12) United States Patent
Zhang

(10) Patent No.: US 12,646,165 B2
(45) Date of Patent: Jun. 2, 2026

(54) CONTOUR EDITING TOOL FOR PROCESSING OCT IMAGES

(71) Applicant: CANON U.S.A., INC., Melville, NY (US)

(72) Inventor: Yu Zhang, Concord, MA (US)

(73) Assignee: Canon U.S.A., Inc., Melville, NY (US)

( * ) Notice: Subject to any disclaimer, the term of this patent is extended or adjusted under 35 U.S.C. 154(b) by 752 days.

(21) Appl. No.: 18/048,255

(22) Filed: Oct. 20, 2022

(65) Prior Publication Data

US 2024/0135529 A1    Apr. 25, 2024
US 2024/0233117 A9    Jul. 11, 2024

(51) Int. Cl.
G06T 7/00       (2017.01)
G06T 7/12       (2017.01)
G16H 30/40      (2018.01)

(52) U.S. Cl.
CPC .............. G06T 7/0012 (2013.01); G06T 7/12 (2017.01); G16H 30/40 (2018.01); G06T 2207/10101 (2013.01); G06T 2207/30101 (2013.01)

(58) Field of Classification Search
None
See application file for complete search history.

(56) References Cited

U.S. PATENT DOCUMENTS 6,459,439 B1    10/2002    Ahlquist et al.
7,801,343 B2    9/2010    Unal et al.

8,754,855 B2    6/2014    Duncan et al.
9,138,147 B2    9/2015    Schmitt et al.
9,557,154 B2    1/2017    Tearney et al.
10,109,058 B2    10/2018    Ambwani et al.
11,287,961 B2    3/2022    Gopinath et al.
11,382,516 B2    7/2022    Wu et al.

(Continued)

OTHER PUBLICATIONS

Ali, Z.A., et al., "Intracoronary optical coherence tomography: state of the art and future directions", Euro Intervention, 2021, pp. 105-139.

(Continued)

*Primary Examiner* — Mark R Milia
(74) *Attorney, Agent, or Firm* — Canon U.S.A., Inc. I.P. Division

(57) ABSTRACT

A method and system for editing a lumen contour of a tomographic image. A method comprises: receiving image data corresponding to a plurality of tomographic images acquired by an imaging catheter scanning a blood vessel; obtaining, by a processor, an automatically-generated lumen contour of the blood vessel from a tomographic image of the blood vessel; displaying, on a display, the automatically-generated lumen contour overlaid on the tomographic image of the blood vessel; identifying a true lumen edge of the blood vessel in the tomographic image; estimating a percentage of matching between a shape of the automatically-generated lumen contour to a shape of the true lumen edge; and receiving editing operations from a user via a touch-screen interface for editing at least part of the automatically-generated lumen contour based on the estimated percentage of matching. Plural editing modes are available based on the percentage of matching meeting one or more thresholds.

22 Claims, 14 Drawing Sheets

(56)                    References Cited

U.S. PATENT DOCUMENTS

| | | | | |
|---|---|---|---|---|
| 11,612,442 B2 * | 3/2023 | Kim | | G06V 10/757 |
| | | | | 600/424 |
| 2010/0166283 A1 * | 7/2010 | Grosskopf | | A61B 6/466 |
| | | | | 382/131 |
| 2011/0071404 A1 | 3/2011 | Schmitt et al. | | |
| 2014/0024930 A1 | 1/2014 | Furuichi et al. | | |
| 2014/0099012 A1 | 4/2014 | Begin et al. | | |
| 2015/0213629 A1 | 7/2015 | Celi et al. | | |
| 2015/0297373 A1 | 10/2015 | Schmitt et al. | | |
| 2016/0228097 A1 | 8/2016 | Jaffer et al. | | |
| 2017/0325712 A1 * | 11/2017 | Gopinath | | G06T 7/73 |
| 2019/0099079 A1 | 4/2019 | Yamada et al. | | |
| 2019/0282199 A1 * | 9/2019 | Merritt | | A61B 8/085 |
| 2019/0298174 A1 | 10/2019 | Watanabe | | |
| 2020/0129147 A1 | 4/2020 | Nair et al. | | |
| 2021/0407098 A1 | 12/2021 | Athanasiou | | |
| 2023/0018499 A1 * | 1/2023 | Blaber | | G06T 7/12 |

OTHER PUBLICATIONS

Athanasiou, L., et al., "Optimized computer-aided segmentation and 3D reconstruction using intracoronary optical coherence tomography", IEEE J Biomed Health Inform., Jul. 2018, pp. 1168-1176, vol. 22, No. 4.

Tearney, G., et al., "Consensus Standards for Acquisition, Measurement, and Reporting of Intravascular Optical Coherence Tomography Studies", Journal of the American College of Cardiology, Mar. 20, 2012, pp. 1058-1072, vol. 59, No. 12.

Amrute. J.M., et al., "Polymeric endovascular strut and lumen detection algorithm for intracoronary optical coherence lomography images", Journal of Biomedical Optics, Mar. 2018, vol. 23, No. 3.

Ughi, G.J., et al., "Dual modality intravascular optical coherence tomography (OCT) and near-infrared fluorescence (NIRF) imaging: a fully automated algorithm for the distance-calibration of NIRF signal intensity for quantitative molecular imaging", Int J Cardiovasc Imaging, Oct. 24, 2014, pp. 259-268, vol. 31 No. 2.

Wang, et al., "Ex vivo catheter-based imaging of coronary atherosclerosis using multimodality OCT and NIRAF excited at 633 nm," Biomedical Optics Express, 2015, pp. 1363-1375, vol. 6, No. 4.

* cited by examiner

CONTOUR EDITING TOOL FOR PROCESSING OCT IMAGES

CROSS-REFERENCE TO RELATED APPLICATIONS n/a

BACKGROUND INFORMATION

Field of Disclosure

The present disclosure generally relates to image processing. More particularly, this disclosure is directed to a system and method for editing medical images acquired from inside a biological lumen via an imaging catheter.

Description of Related Art

Optical coherence tomography (OCT) imaging is an interferometric imaging technique that uses constructive interference of coherent light to provide high-resolution, cross-sectional information of tissue microstructures in situ and in real-time. In OCT imaging, a laser beam scans across the tissue surface of a sample to acquire a two-dimensional (2D) image line-by-line. This technique is commonly used in ophthalmology, cardiology, gastroenterology and other fields of medicine. For cardiovascular applications, a light beam is transmitted through a fiber-optic based imaging catheter that is inserted into the coronary arteries of a patient. The light beam is emitted from the catheter distal end, and scanned along the vessel wall in a rotary fashion, while the catheter is pulled back through the artery to collect image data of the vessel wall over a distance of about 5-10 centimeters (cm). Image processing of the collected data can show complex coronary conditions and vessel-wall pathologies such as atherosclerosis or stenosis, with an axial resolution of approximately 10 microns ($\mu$m) or less and a lateral resolution of at least 20 microns. However, OCT has relatively low penetration depth (0.1-2.5 millimeters (mm)) with strong dependence on tissue optical properties, which limits proper identification of the vessel outer border (intima- or plaque-media interface). For example, detection and quantification of types of plaque and macrophages (an indicator of inflammation), quantification of calcified lesions, such as their locations and volumes, can provide valuable information, for example, for optimal placement of coronary stents. Further, detection and quantification of structures such as stents can help evaluate risks of malaposition and uncovered struts associated with thrombosis.

Intravascular fluorescence is a catheter-based molecular imaging technique that uses laser light to stimulate fluorescence emission from a vessel wall and/or from plaque components within a particular vessel. Light in the near-infrared wavelength range is often used to stimulate fluorescence emission from a vessel wall. Similar to OCT, imaging catheters used in intravascular fluorescence contain an optical fiber to deliver and collect light to and from the lumen of a vessel wall. Fluorescence may include near-infrared auto-fluorescence (NIRAF) generated by endogenous fluorophores, or near-infrared fluorescence (NIRF) generated by molecular agents injected intravenously in the vessel. Fluorescence detection can be obtained by mathematical integration of the emitted intensity of fluorescence over a short period of time, by measuring the life-time of the fluorescence signal (i.e., fluorescence-lifetime imaging microscopy or FLIM), or by analyzing the spectral shape of emitted fluorescence (fluorescence spectroscopy).

The combination of OCT and fluorescence imaging modalities into a single imaging catheter provides a multi-modality OCT system (MMOCT system) with the capability to simultaneously obtain co-localized and core-registered morphological and molecular information from a biological lumen such as blood vessels. See, for example, publications by Wang et al., (herein "Wang") entitled "*Ex vivo catheter-based imaging of coronary atherosclerosis using multimodality OCT and NIRAF excited at 633 nm*," Biomedical Optics Express 6(4), 1363-1375 (2015); Ughi et al., (herein "Ughi") entitled "*Dual modality intravascular optical coherence tomography (OCT) and near-infrared fluorescence (NIRF) imaging: a fully automated algorithm for the distance-calibration of NIRF signal intensity for quantitative molecular imaging. Int J Cardiovasc Imaging.* 2015 February; 31(2):259-68; and patent-related publications including U.S. Pat. No. 9,557,154, US 20160228097, US 20190099079, and US 20190298174, among others.

In a MMOCT system, vessel wall (lumen edge) detection and appropriate issue characterization depends on several factors such as detected signal strength, the distance between the catheter and the lumen edge (the "lumen distance"), and/or the diameter or cross-sectional area of a vessel wall or vessel lumen. In the current state of the art, automatic lumen detection based on known algorithms is chiefly relied upon to determine the signal path length from catheter to lumen to establish the lumen edge in an OCT/NIRAF image. However, due to catheter movement inside the lumen, the position of the catheter with respect to the lumen is highly variable. Finding high quality contours that outline a tubular structure from a collection of cross sections may be problematic, as tubular structures may not exhibit a large gradient magnitude at their borders. In addition, tubular structures may contain bifurcations, trifurcations, or more complex branch structures that make finding high quality contours difficult. In using the results from contouring, it is possible that the contour produced at a branching of the vessel may be identified as a false positive for an aneurysm or stenosis, or may otherwise obscure important details.

Therefore, reliance on automatic lumen detection can potentially lead to lower fidelity NIRAF and/or OCT signals, which can lead to erroneous diagnosis and/or subpar treatment.

To improve accuracy of lumen edge detection, contour editing methods are known in related art such as intravascular ultrasound (IVUS) imaging. See, for example, pre-grant publication US 2020/0129147 A1 by Nair et al., (Nair). Conventional contour editing methods often include manipulating the contour shape by assigning a list of control points to the contour shape of the lumen edge, and manually dragging the contour points in one or more directions (e.g., by "click and drag" operation of a mouse, as taught by Nair). Manual tracing of the lumen contours is laborious and time consuming given the large number of images acquired in a typical OCT examination (i.e., usually hundreds or thousands in a single pullback). Therefore, the manual editing approach offers a limited solution that can be difficult and time-consuming, and may also be subject to user error. Specifically, often when the discrepancy between the original contour and the desired results is large, the user might have to move many control points per image, which can be burdensome and tedious to the user. In addition, the control point movement could affect an unexpected range of the contour shape, which makes the desired results hard to achieve.

For the user, it is important to be able to interact with the system in a way that does not interfere with the clinical workflow, e.g. during a surgery. Touch interfaces, such as tablets and large touchscreen displays provide a more convenient way to implement the contour editing in a clinical workflow. The term "touchscreen" generally refers to a display screen that is responsive to touch by a person's fingers and typically, fingertips. Touchscreens are well known in the art and have replaced keyboard/mouse entry devices and conventional display screens in a wide variety of commercial, industrial and medical equipment. Touchscreen interfaces may be fixed, or mounted on a movable arm, next to an operation table or patient's bed. The user can interact with a touchscreen even when wearing surgical gloves (when specialized gloves are provided). There are, however, additional issues and challenges introduced by touchscreen interfaces. For example, lack of touch location accuracy is often observed.

Therefore, there remains a need to provide an improved system and method which allows accurate user interaction for contour editing of vessel images or the like.

SUMMARY OF EXEMPLARY EMBODIMENTS

According to at least one embodiment, the present disclosure provides a method and system for editing a lumen contour of a tomographic image of a vessel. In one embodiment, a method comprises: receiving, by a processor, image data corresponding to a plurality of tomographic images acquired by an imaging catheter scanning a blood vessel; obtaining, by the processor, an automatically-generated lumen contour of the blood vessel within a tomographic image of the blood vessel; displaying, on a touchscreen display, the automatically-generated lumen contour overlaid on the tomographic image of the blood vessel; identifying a lumen edge of the blood vessel within the tomographic image; estimating, by the processor, a percentage of matching between a shape of the automatically-generated lumen contour to a shape of the identified lumen edge; and receiving editing operations on a user interface for editing at least part of the automatically-generated lumen contour based on the estimated percentage of matching.

According to another embodiment, the system comprises: an imaging catheter configured to be inserted into a blood vessel to guide radiation of two or more wavelengths to a vessel wall, and configured to collect backscattered radiation in response to irradiating the vessel wall with a radiation of first wavelength and collect a fluorescence signal emitted by the vessel wall in response to irradiating the vessel wall with a radiation of second wavelength different from the first wavelength. A processor is configured to: receive image data corresponding to a plurality of tomographic images acquired by the imaging catheter scanning the blood vessel; automatically-generate a lumen contour of the blood vessel within a tomographic image of the blood vessel; display, on a touchscreen display, the automatically-generated lumen contour overlaid on the tomographic image of the blood vessel; identify a lumen edge of the blood vessel within the tomographic image; estimate a percentage of matching between a shape of the automatically-generated lumen contour to a shape of the identified lumen edge; and receive editing operations on a user interface for editing at least part of the automatically-generated lumen contour based on the estimated percentage of matching.

These and other objects, features, and advantages of the present disclosure will become apparent upon reading the following detailed description of exemplary embodiments of the present disclosure, when taken in conjunction with the appended drawings, and provided claims.

DETAILED DESCRIPTION OF EXEMPLARY EMBODIMENTS

Figure 1A:
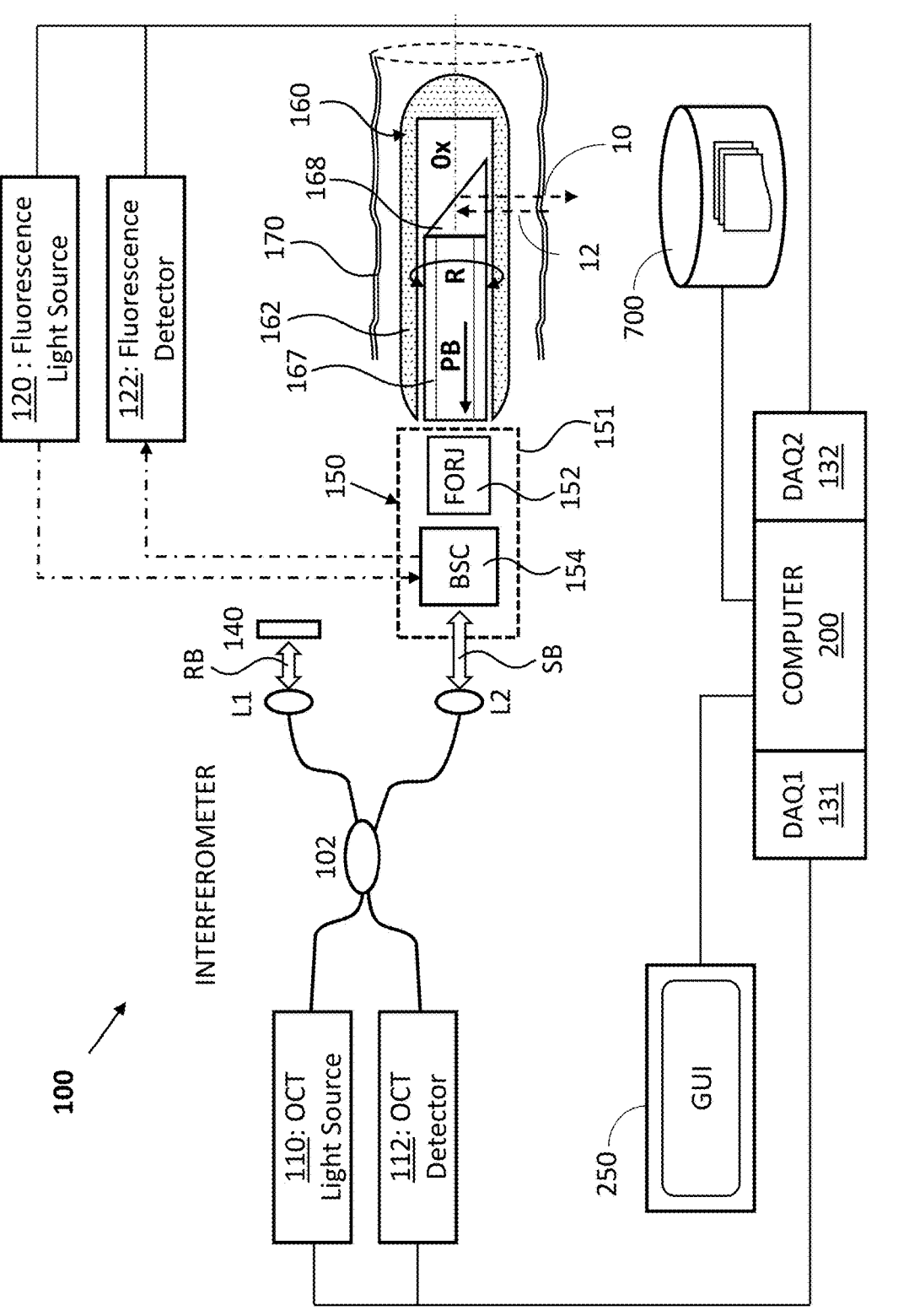
FIG. 1A illustrates an exemplary multimodality OCT (MMOCT) system 100 including a fluorescence modality and an OCT modality using a single fiber-based imaging catheter 160.

Before the various embodiments are described in further detail, it is to be understood that the present disclosure is not limited to any particular embodiment. It is also to be understood that the terminology used herein is for the purpose of describing exemplary embodiments only, and is not intended to be limiting. Unless defined otherwise, all technical and scientific terms used herein have the same meaning as commonly understood by one of ordinary skill in the art.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to be inclusive of end values and includes all sub-ranges subsumed therein, unless specifically stated otherwise. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

Unless specifically stated otherwise, as apparent from the following disclosure, it is understood that, throughout the disclosure, discussions using terms such as "processing," "computing," "calculating," "determining," "displaying," or the like, refer to the action and processes of a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computer or electronic operations described in the specification or recited in the appended claims may generally be performed in any order, unless context dictates otherwise. Also, although various operational flow diagrams are presented in numbered blocks or sequence(s), the numbering is used for convenience only. It should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to", "in response to", "related to", "based on", or other similar past-tense adjectives are generally not intended to exclude such variants, unless context dictates otherwise.

The present disclosure generally relates to medical devices, and it exemplifies embodiments of an optical probe applicable to an optical coherence tomographic (OCT) imaging catheter, a fluorescence imaging catheter, or a combination of such apparatuses (e.g., a multi-modality catheter having a single optical probe). The embodiments of the optical probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic site. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding. The refraction index of the core is larger than the refraction index of the cladding. Depending on design choice some fibers can have multiple claddings surrounding the core.

Although the present disclosure proposes certain illustrative embodiments of systems and methods of lumen editing based on manual lumen detection to improve measurement of optical parameters within selected regions of interest, other embodiments may include alternatives, equivalents, and modifications. Therefore, certain particular features may not be essential to implement or practice the apparatuses, systems, and/or methods described herein.

<MMOCT System>

FIG. 1A illustrates an exemplary multimodality imaging system 100 (hereinafter referred to as "system 100"). The system 100 includes an OCT imaging modality and a fluorescence imaging modality using a shared fiber-based imaging catheter 160. The system 100 can be used as an intravascular imaging system configured to acquire images of a vessel including coronary arteries or cerebral arteries. The system 100 may also be adapted with a balloon catheter or other appropriate structure to be used for examining or treating other bodily lumens, such as trachea, bronchus, alveoli or similar.

As depicted in FIG. 1A, the OCT modality includes an interferometer (e.g., a Michelson interferometer) having a sample arm and a reference arm, an OCT light source 110, an OCT light detector unit 112, a first data acquisition board (DAQ1) 131, and a computer system 200. The sample arm includes an optical system L2 (an optical fiber and a lens), a patient interface unit (PIU) 150, and the catheter 160. The reference arm includes an optical system L1 (an optical fiber and a lens), and a reflector 140. In the case of Time Domain OCT (TD-OCT) imaging, the reflector 140 may be implemented as a scanning mirror. And, in the case of Frequency Domain OCT (FD-OCT) imaging, the reflector 140 may be implemented as a stationary mirror. The fluorescence modality includes an excitation light source 120, a fluorescence detector 122, the PIU 150, the catheter 160, a second data acquisition board (DAQ2) 132, and the computer system 200. In other words, the OCT modality and the fluorescence modality share the same fiber-based imaging catheter 160. The computer system 200 is connected to a display device 250 and to an external system such as a picture archiving and communication system (PACS) 700. The PIU 150 includes a beam splitter/combiner (BSC) 154, a fiber optic rotary joint (FORJ) 152, and a pullback unit 151 (e.g., a precision linear stage).

In one embodiment, the system 100 may use a swept-source laser (1310 nm+/−50 nm) as the OCT light source no for the OCT modality, and a Helium-Neon (He—Ne) laser with a center wavelength of about 633 nm as the excitation light source 120 for the fluorescence modality. The OCT detector 112 can be a balanced photodetector implemented as either an array of photodiodes, a photo multiplier tube (PMT), a multi-array of cameras, or other similar interference pattern detecting device. The fluorescence detector 122 may include a photodetector configured to detect intensity of a fluorescence signal.

The catheter 160 includes an imaging core comprised of a torque coil (not shown), a double clad fiber (DCF) 167, and a distal optics assembly 168. The imaging core is enclosed in a protective sheath 162. The protective sheath 162 has an inner diameter that extends from a proximal end to a distal end. All catheter components including the imaging core and sheath are arranged substantially concentric to a catheter axis Ox. The distal optics assembly 168 may include a polished ball lens at the tip of the DCF 167 for side-view imaging. The distal optics assembly 168 may alternatively include a graded index (GRIN) lens and a beam directing component (e.g., a mirror, grating or a prism) attached to the tip of the DCF 167. At the proximal end of the sheath 162, the catheter 160 is removably connected to the PIU 150 via a catheter handle or connector (not shown). The catheter 160 is configured to be inserted into a blood vessel 170 (e.g., an artery or a vein). To that end, the catheter 160 may be guided over a guidewire until the distal end of the catheter reaches just beyond the region of interest (e.g., stenosis).

In operation, the system 100 is configured to acquire co-registered OCT and fluorescence images from the vessel 170. To that end, the PIU 150 is controlled by the computer 200 to simultaneously deliver an incident beam 10 and collect a returning beam 12 to/from the vessel 170 via the catheter 16o. The incident beam 10 includes near infrared light (a radiation of first wavelength) emitted from the OCT light source 110, and excitation light (a radiation of a second wavelength) emitted from the excitation light source 120.

The OCT modality measures the time delay of light that is reflected or backscattered from tissue of the vessel 170, and that is collected by the catheter 16o, by using a technique known as interferometry. In this technique, light from the OCT light source 110 is split into a sample beam and a reference beam. The sample beam travels to a region of interest inside the patient via the sample arm (through the catheter), and the reference beam travels a predetermined distance to the reflector 140 via the reference arm. The sample beam is guided through the sample arm via the optical system L2, the BSC 154, the FORJ 152 to the catheter 160. In the catheter 160, light travels through the core of DCF 167, and is directed by the distal optics 168 towards the vessel 170. At the same time, the reference beam RB is guided through the reference arm to the reflector 140 via the optical system L1.

Light reflected, scattered and/or emitted by the vessel 170 (i.e., return beam 12) is collected by the distal optics 168, and travels in a reverse optical path through the DCF 167.

Specifically, an OCT signal corresponding to light scattered or reflected by the vessel 170 travels through the core and/or cladding of DCF 167; and a fluorescence signal corresponding to fluorescence emitted from the vessel 170 travels through the cladding of DCF 167. The BSC 154 guides the OCT signal to the fiber splitter 102, and guides the fluorescence signal to the fluorescence detector 122. At the fiber splitter 102, the light scattered or reflected by the vessel 170 is recombined with light of the reference arm (RB). From the fiber splitter 102, the recombined light is detected by the OCT light detector 112. The OCT light detector 112 will output an analog signal (interference pattern signal) corresponding to the intensity of an OCT interference signal (i.e., interference between the sample beam and the reference beam). Here, it should be recalled that an interference pattern is generated by in interferometer only when the optical path length of the sample arm roughly matches the path length of the reference arm within the coherence length of the OCT light source 110. In some embodiments, to ensure the optical path lengths of the sample and reference arms match, the sample arm may include an optical delay line (not shown).

Under control of the computer 200, the PIU 150 controls rotation and pullback of the imaging core of catheter 16o to scan the vessel 170 with the incident beam 10 in a helical scanning manner. Rotation of the imaging core is shown by arrow R, and pullback movement is shown by arrow PB. The return beam 12 is collected by the distal optics 168 arranged at the distal end of the catheter 160, and the collected light is transmitted back through the DCF 167 to the PIU 150. From the PIU the collected light (sample beam) advances to the OCT detector 112 via the optical system L1 and the fiber splitter 102. The interference signals output from the OCT detector 112 are pre-processed by data acquisition board (DAQ1) 131, and transferred to the computer 200. The computer 200 performs signal processing to generate OCT images in a known manner.

In the fluorescence modality, excitation light suitable for generating fluorescence from vessel 170 is emitted from the excitation light source 120, and guided to the vessel 170 via the BSC 154 and the catheter 160. A fluorescence signal emitted from the vessel 170 is collected via the catheter 160, and delivered to the fluoresce detector 122. The computer system 200 uses the OCT interference signal and/or the fluorescence signal to generate an image of the vessel 170. In the fluorescence modality, the excitation light source 120 emits excitation light with a center wavelength of 633 nm (radiation of second wavelength) to irradiate the vessel 170 through the PIU 150 and the distal optics of catheter 160. In response to being irradiated by the excitation light, the vessel 170 emits near infrared auto-fluorescence (NIRAF signal) or near infrared fluorescence (NIRF signal) with broadband wavelengths of about 633 to 800 nm (radiation of third wavelength) based on known fluorescence emission principles. As used herein, fluorescence is an optical phenomenon in which the molecular absorption of energy in the form of photons triggers an immediate emission of fluorescent photons with a longer wavelength.

In one embodiment, the fluorescence signal generated by the vessel 170 may include auto-fluorescence, which is the endogenous fluorescence light generated without application of a dye or an agent. In other embodiments, the fluorescence signal generated by the vessel 170 may include fluorescence light generated by exogenous fluorescence of dye or contrast agents intravenously added to the lumen sample. The auto-fluorescence (or fluorescence) light is collected by the distal optics 168 of the catheter 160, and delivered back to the PIU 150, where the FORJ 152 and a non-illustrated beam combiner/splitter guides the fluorescence signal to a detector 122. The fluorescence signal (fluorescence intensity signal) output from detector 122 is digitized by data acquisition (DAQ) 132 and transmitted to the computer system 200 for image processing. Preferably, the OCT interference patterns of the OCT modality and the fluorescence signal from the fluorescence modality are co-registered in terms of time and location.

Figure 1B:
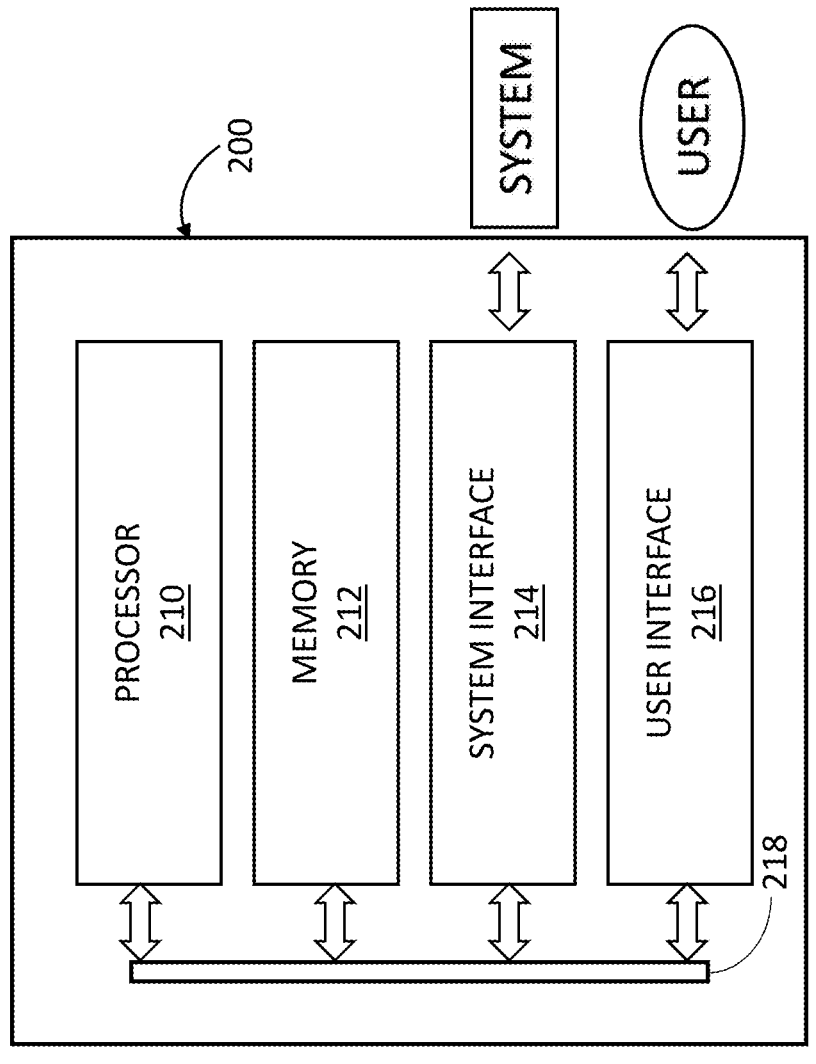
FIG. 1B illustrates components of a computer Zoo.

FIG. 1B shows a schematic diagram of computer 200, according to embodiments of the present disclosure. Computer 200 refers to any machine that operates to accept a structured input, processes the structured input according to prescribed rules (a program), and produces one or more results as output. The computer 200 may include one or more than one processor 210; a memory module 212, a system interface module 214, and a user interface module 216. The various functional components of the computer 200 are operatively connected and communicate with each other via physical and/or logical data lines, such as a DATA BUS 218.

The processor 210 may include a central processing unit (CPU), a digital signal processing (DSP) circuit, an application-specific integrated circuit (ASIC) board, a proportional integral derivative (PID) controller, a field programmable gate array (FPGA) board, a general-purpose computing device, or any combination thereof, and/or other related logic devices, cloud-based and quantum computers. The processor 210 may also comprise a combination of a hardware device, a firmware device, and a software device (cloud-based processor) configured to perform the operations described herein. Furthermore, the processor 210 may be implemented as a combination of computing devices, e.g., a combination of a DSP board and a microprocessor, a plurality of microprocessors, one or more microprocessors in conjunction with FPGA board, or any other such configuration.

Memory module 212 may include one or more non-transitory computer-readable and/or writable media. The memory module 212 may include a cache memory (e.g., a cache memory for processor 210), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. The memory module 212 may store computer-executable instructions that, when executed by the processor 210, cause the processor to perform the operations described herein. Memory module 212 may store instructions including Operating System (OS) programs, and control and processing programs. Instructions may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The system interface 214 provides an electronic interface (electronic connection circuits) for one or more of the OCT light source 110, the OCT detector 112, the DAQ1 131, the excitation light source 120, the fluorescence detector unit 122, the DAQ2 132, as well as the PIU 150. The system interface 214 may include programmable logic for use with a programmable logic device (PDL), such as a Field Programmable Gate Array (FPGA), or other discrete components, integrated circuits or combination thereof. The system interface 214 may include communication cables and/or a network connections for connecting the computer 200 with other devices (e.g., PACS 700), such connections can be either wired or wireless.

The user interface 216 provides a communication interface (electronic connections) for input/output (I/O) devices used by the user to control the system. I/O devices may include a keyboard, a display device 250 (e.g., an LCD or LED or OLED display), a pointing device (mouse or trackball), a touch interface (touchscreen), a scanner, a microphone, a camera, a printing device, etc. The functions of the user interface 216 and of the system interface 214 may be realized, at least in part, by computer-executable instructions (e.g., one or more programs) recorded in memory module 212 and executed by processor 210, or programs executed in a remote location via a network (e.g. cloud computing). According to at least one embodiment, display device 250 is a touchscreen display, such as a capacitive touchscreen capable of detecting where the user has pressed the screen surface. An example of touchscreen technology is described in U.S. Pat. No. 7,844,915 B2, which is incorporated by reference herein for all purposes. In other embodiments, the touchscreen can be implemented by different sensing technologies including, for example, Wire Resistive, touchless Surface Capacitive, Projected Capacitive (P-Cap), SAW (Surface Acoustic Wave), and IR (Infrared). Touchless user interface (UI) technology provides users with a simple and intuitive way of using touchscreen displays without having to physically touch the screen. UI technology recognizes a finger as it moves towards a point on the screen. At a certain distance from the screen, a specific action is triggered by the UI software. Equivalent to the traditional touchscreen, various actions such as tapping and swiping can be used intuitively by holding and/or moving the user's finger near the screen (without touching it).

As previously mentioned in the Background section, an MMOCT system, i.e., OCT-NIRAF system, can be used to acquire OCT and/or fluorescence images of coronary arteries in a patient's vasculature, where for each A-line of OCT signal, a NIRAF signal is also collected and stored in correspondence to the A-lines. Referring back to FIG. 1A, the pullback movement PB combined with rotational movement R of the catheter 160 enables A-lines to be generated multiple times by helically scanning the inner surface of vessel 170. Two dimensional (2D) images of vessel 170 are formed by combining the plurality of A-line scans acquired during a pullback. Each 2D image of an artery cross section may be formed by approximately 500 A-line scans, corresponding to a full circumferential (360 degree) scan of the vessel by the catheter 160. This full circumferential scan is sometimes referred to as a "frame" or a B-scan. Three-dimensional (3D) imaging of the vessel 170 can be achieved by combining a plurality of 2D images (a plurality of B-scan frames) obtained during the pullback operation. The resulting catheter scan acquired during a pullback includes successive A-line scans combined to form 2D B-scans which in turn can be combined into a full 3D dataset (or C-scan) of the vessel 170. Data collected from successive A-line scans is processed (e.g., by fast Fourier transformation and other known algorithms) to generate OCT images of the vessel 170 in a known manner. At the same time, the fluorescence signal (e.g., an intensity value) is also collected, processed (digitized and calibrated), displayed, and analyzed in correspondence with the OCT images.

Here, it is important to recall that as a light beam encounters a boundary between layers of tissue (tissue interface) with different refractive indices (optical impedances), a portion of the light is scattered, and a portion is transmitted. OCT measures light that is reflected or backscattered from the tissue interface, and is collected by the catheter 160. The amount of backscattered light, and therefore the intensity of the OCT image signal, is dependent on the magnitude of the difference in refractive indices of the vessel tissues. For large planar structures with dimensions that are larger than the wavelength of the incident light beam, such as stent struts, the reflected light is higher when the object is perpendicular to the direction of the incident beam 10. As light of the incident beam passes through layers of vessel tissue, light is attenuated by scattering and absorption. Highly attenuating tissue, such as lipid-rich tissue, has a low penetration depth, and therefore, OCT light does not travel deep within some lipid-rich tissue (e.g., plaque). Other tissues, such as collagen and calcium, have lower attenuation, and as a result, OCT light can travel deeper into these tissues. For this reason, the penetration depth of OCT light in vessels depends on tissue type and usually ranges from about 0.1 to 2.0 mm when using typical near infrared light with wavelengths center around 1300 nm. In addition, it should be recalled that OCT light cannot image through blood because red blood cells (RBCs) attenuates the OCT light before it reaches the artery wall. Therefore, OCT images are acquired as blood is flushed from the field of view of the catheter.

The data (OCT data and fluorescence data) collected by the system 100 is processed by computer 200 to reconstruct one or more images of the tissue structures. The images are stored in onboard memory 212 of computer 200 or in PACS 700.

An important feature in the MMOCT system is to display the automatically detected lumen edge contour on top of the OCT tomographic view image to be able to analyze and determine the true morphology of the arterial wall. Due to the complex nature of the OCT data and limitation of the algorithm, the lumen edge contour may be different from the lumen border, and mismatch with the underneath image often occurs. The present disclosure provides a lumen contour editing tool so that a user can easily adjust the contour to the true shape of the lumen edge, or the user can focus on a specific section of the contour and easily adjust the contour section to the true shape of the lumen edge. The contour editing tool allows for necessary measurements conducted on the lumen contours such as the lumen contour area or diameters to be edited/adjusted more effectively.

<Graphical User Interface (GUI)>

The results of pullback and image recording operations are typically displayed "as detected" for a user to evaluate the results. The display of fluorescence data (NIRAF or NIRF) and OCT data is automatically generated based on algorithmic processing techniques for overlaying the OCT and fluorescence data in predetermined formats. Catheter based multimodality imaging results can be shown as a ring of fluorescence data arranged to surround the OCT tomographic view, and/or can be displayed to show the OCT and fluorescence data overlaid in longitudinal view (sometimes called carpet view).

Figure 2A:
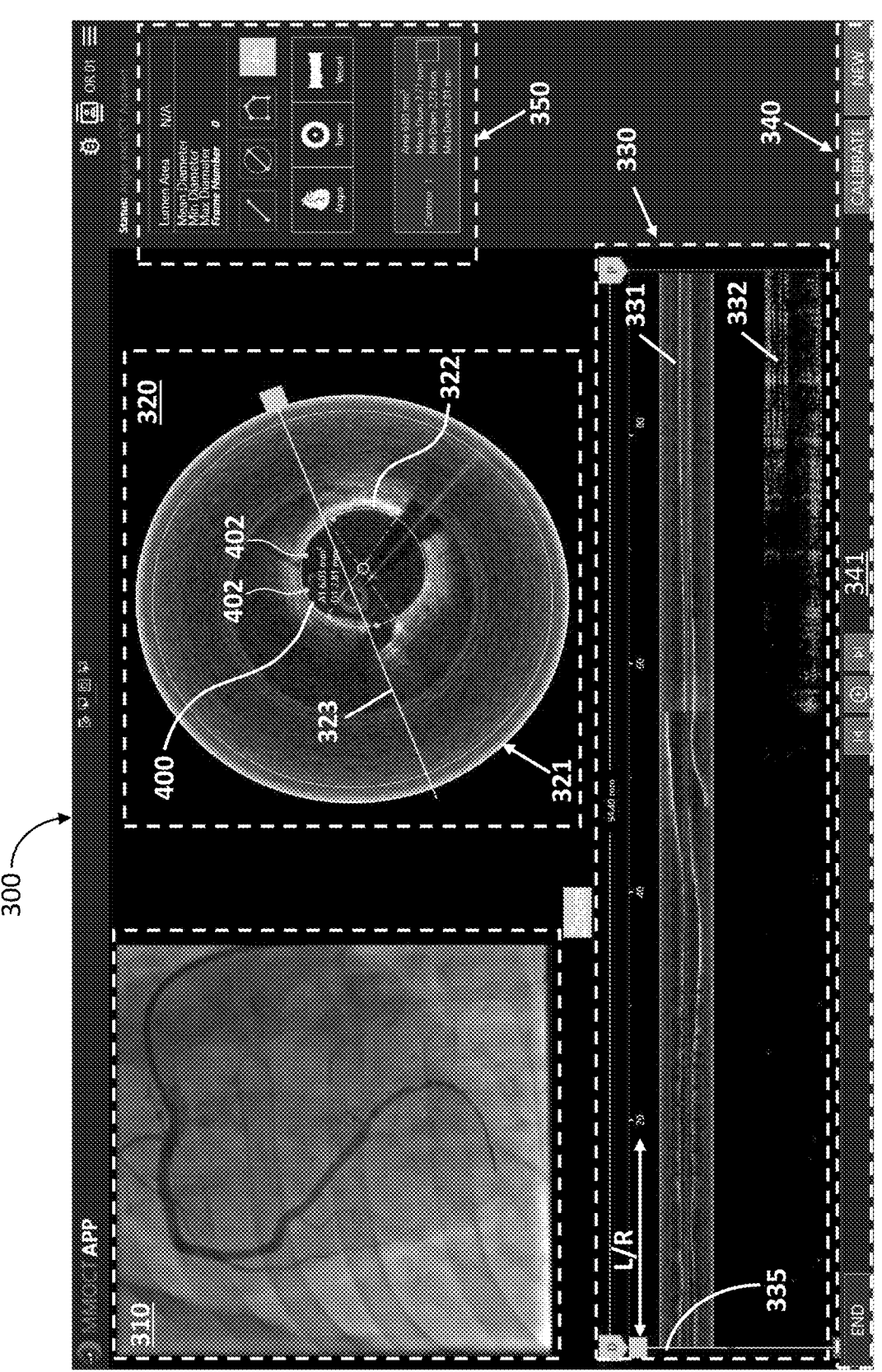
FIG. 2A illustrates a graphical user interface (GUI) 300 configured to display a plurality of images of a vessel, and to enable a user to evaluate and/or edit a lumen contour 400 displayed overlaid on top of a tomographic image 321.

FIG. 2A illustrates a graphical user interface (GUI) 300 configured to display a plurality of images of a vessel, and to enable a user to evaluate and/or edit a lumen contour 400 displayed overlaid on top of a tomographic image 321. FIG. 2A illustrates an exemplary output displayed on the screen of display device 250. The GUI 300 is divided into a plurality of sections including a first image-display section 310, a second image-display section 320, a third image-display section 330, a display control section 340, and an editing control section 350. It will be appreciated GUI 300 may have a higher or lower number of sections.

The first display section 310 is configured to display a first image generated by an external imaging modality (an auxiliary imaging modality), such as fluoroscopy or computed tomography (CT). The second display section 320 is configured to display a tomographic image 321 (Tomo view) of the vessel 170 acquired by the MMOCT catheter 160. In the tomographic image 321, the true lumen edge 322 represents the actual lumen wall (e.g., vessel wall) detected by the OCT system. A computer generated lumen contour 400, including a plurality of controls points 402, is automatically added (overlaid) on the tomographic image 321 based on well-known contour generating algorithms. The third display section 330 is configured to display an OCT longitudinal view (a vessel view in L-mode) 331 and a fluorescence carpet view 332 of the vessel 170. The OCT vessel view 331 is taken along orientation of line 323 shown in the tomographic image 321. The display control section 330 allows the user to change the location of the tomographic image 321, by moving a vertical marker 335 left to right (L/R) along the length of the vessel view 331. That is, the vertical marker 335 is associated with current tomographic image 321 shown in the second display section 320. The display control section 340 also allows the user to "play" a recorded image of the vessel 170, using control display tools 341 (e.g., stop, play, forward, reverse, etc.). The editing control section 350 is configured to receive inputs from the user to enter an editing mode to edit a lumen contour 400 of the tomographic image 321.

Figure 2B:
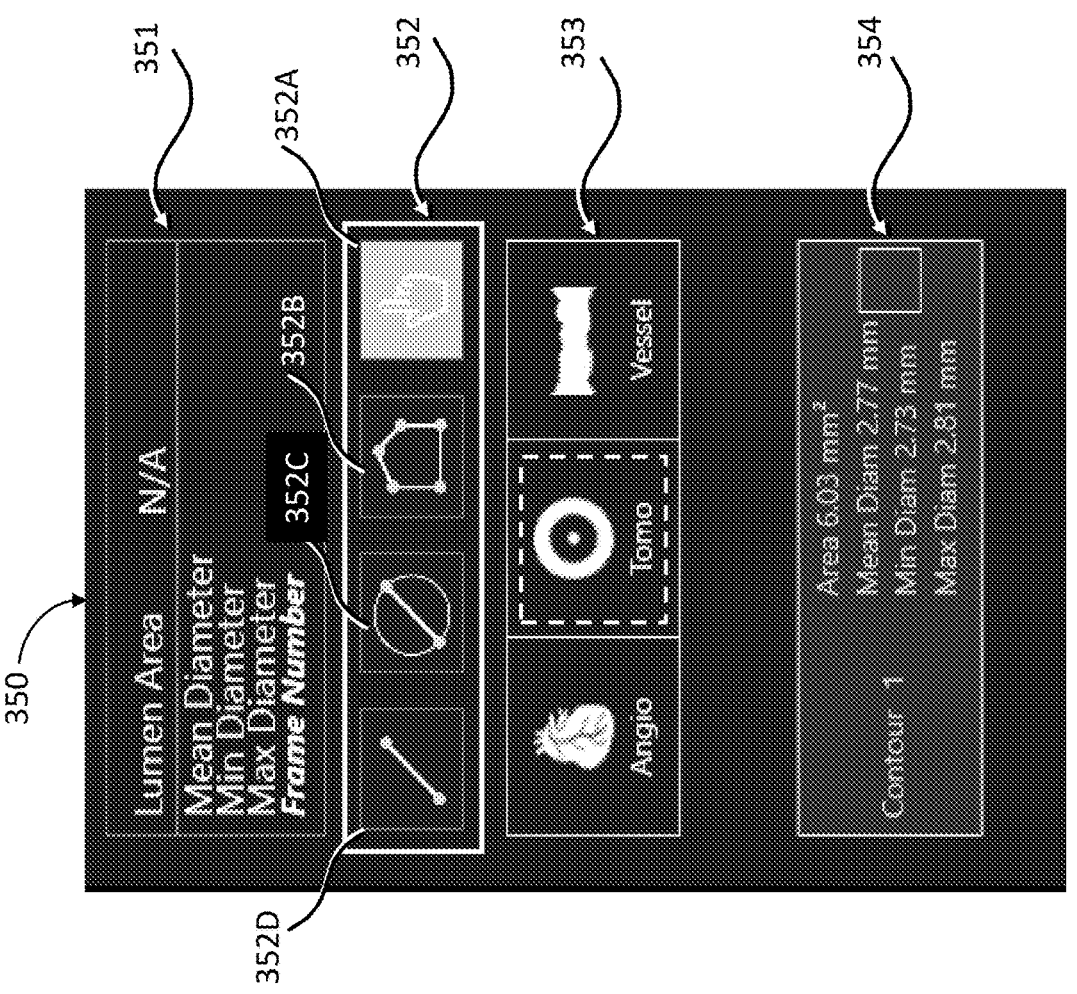
FIG. 2B shows an editing control section 350 of the GUI 300.

FIG. 2B shows an embodiment of the editing control section 350. The editing control section 350 includes a lumen-area information section 351, a tool-selecting section 352, a format-display selecting section 353, and an active contour-measurement display section 354. The format-display selecting section 353 allows the user to select whether an angiographic view (Angio), a tomographic view (Tomo), or a vessel view (Vessel) is actively controlled to evaluate the imaging results. The lumen-area information section 351 and the active contour-measurement display section 354 display measured parameters including lumen area, vessel diameter, and frame number in which the parameters are measured, etc. More specifically, during a contour editing process in which the user is using editing mode to modify the lumen contour, the lumen-area information section 351 displays the original (previously acquired) lumen contour's measurements, while the active contour-measurement display section 354 keeps updating and follows the edited lumen contour's measurements. This gives the user additional information to confirm and accept the edited results to replace the original lumen.

During review of the acquired images, the user needs to place the system in contour editing mode to be able to make contour modifications. When reviewing the lumen contours in regular review mode, the editing mode is not active by default. Once the user decides to edit a certain contour, the user can operate one or more of the contour editing tools 352A, 352B, 352C, 352D, etc., by, for example, selecting one or more of the contour editing tools. Contour editing tools may include predefined tools, such as a drawing tool 352A, a group editing tool 352B, a segment editing tool 352C, a control point editing tool 352D. In response to the user selecting a contour editing tool (any of 352A-352D), the system enters the editing mode. In editing mode, the user is expected to interact with the GUI directly by touchscreen operations using one or more fingers (i.e., without a conventional mouse). It is noted that some mouse-controlled functions are still optionally available to simulate finger touch on the screen, but the mouse-controlled functions do not provide multi-touch capability like touchscreen interaction. Therefore, some gestures supported by the editing tool need to be simulated differently when the user operates the mouse for contour editing. One of the advantages offered by the present disclosure is that the editing tool makes things easier for the user to handle various contour-correction operations with just a few intuitive simple touchscreen interactions, including add or remove control points, drag and release of curve segments, draw one or more new curve segments directly on top of the tomographic view, and/or delete (remove) the automatically generated lumen contour and replace it with a manually defined lumen contour.

Figure 3:
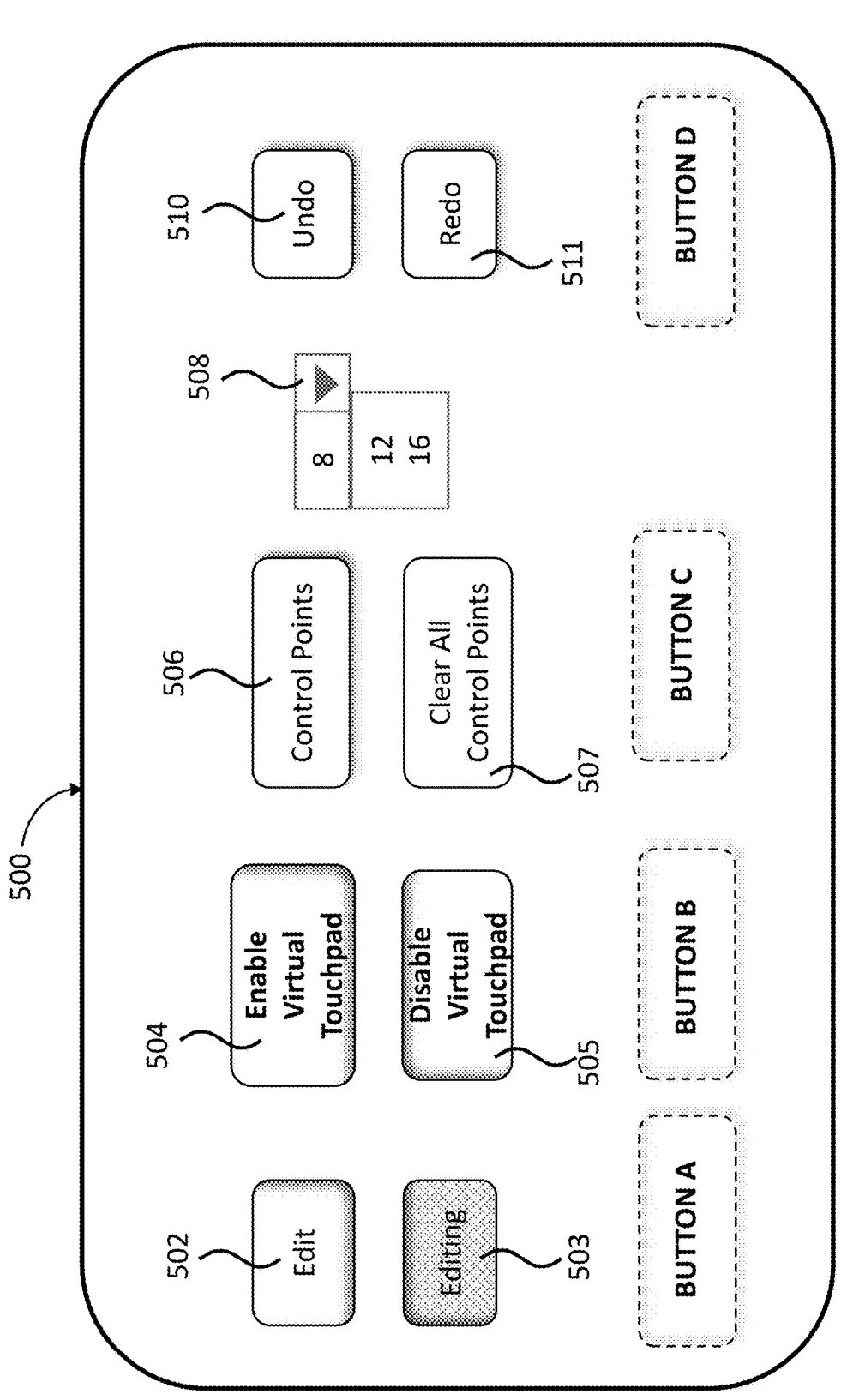
FIG. 3 shows a screen 500 with a plurality of buttons used in the editing mode.

FIG. 3 shows a screen 500 with a plurality of buttons used in the editing mode. When the user touches one or more of the contour editing tools 352A-352D, the system processor 210 causes the display device 250 to output the screen 500. Screen 500 displays setting for GUI 300 including an "Edit" button 502, an "Editing" button 503, an "Enable Virtual Touchpad" button 504, a "Disable Virtual Touchpad" button 505, a "Control Points" button 506, a "Clear all Control Points" button 507, a pulldown button 508, an "Undo" button 51o, an a "Redo" button 511. Additional buttons (BUTTON A, BUTTON B, BUTTON C, BUTTON D, etc.) can be provided according to the needs of the editing process. The functionalities of buttons A-C can be related to the buttons or states already displayed above them in FIG. 3, so that these buttons form certain button groups that are named as A/B/C and D, which will be further described below.

In screen 500, the user enters the editing mode by pressing the "Edit" button 502. Upon entering the editing mode, the "Editing" button 503 changes its color (e.g., becomes green) to inform the user that the system is in editing mode. Under the editing mode, the user can choose to edit the lumen contour 400 by adding control points. To that end, the user may press the "Control Points" button 506. Here, the button groups switch from button A to button C in the form that when "Edit button 502" is pressed down and turn into depressed "Editing button 503", the Control Points button 506 becomes enabled. Upon enabling the "control points" button 506, the system activates the pulldown button 508. With pulldown button 508, the user can choose the number of control points that the user intends to add, delete or modify. In the case that the user decides that control points need to be removed, the user can remove all control points at once by pressing the "Clear All Control Points" button 507. In one embodiment, the "Control Points" button 506 and "Clear All Control Points" button 507 are two separate buttons under "Button C" group. For "control points" button 506, even if there are already control points displayed on the algorithm-generated contour 400, the user can still change the total number of control points using pulldown button 508, and then clicking the "Control Points" button 506 again, so that the system will discard of existing control points, and replace with a predetermined number of new control point redistributed on the contour based on new parameters on the contour. In addition, while control points are present on contour 400, the user can click the "Clear All Control Points" button 507 to remove all of them. If the user is not satisfied with the existed contour, and wants to remove the contour in order to redraw the contour using Mode C as mentioned below, the user can click the "Clear All Control Points" button 507 again and this time, the contour will be removed for the state ready for using editing Mode C.

The buttons related to setting the number of control points belong to Button C group. Button C serves as a state snapshot button that can save the current state of number of available Control points. While after the user chooses to Clear All Control Points, Button C allows the user to recover the last saved state when user clicks it under the condition that no control points are available. To be able to iteratively compare various editing options, the user can undo each operation by pressing the "Undo" button 510, or can repeat a given editing operation by pressing the "Redo" button 511. These two buttons are separate buttons and they belong to Button D group which are related to managing the undo or redo states of the editing process. The buttons will be enabled as soon as the undoable or redoable states are available in stacks. Button D serves as a reset button to both undo and redo states' stacks. To be able to use drag and draw options, the user can interactively enable or disable a virtual touchpad function by respectively touching either the "Enable Virtual Touchpad" button 504 or the "Disable Virtual Touchpad" button 507. Although drawn as two buttons in FIG. 3, the button 504 and button 505 can be a single button with two states, e.g., an un-pressed state corresponds to the "Enable Virtual Touchpad" button 504, and a pressed state corresponds to the "Disable Virtual Touchpad" button 505, or vice versa, respectively. Normally the default mode of the Virtual Touchpad is not enabled, or is used only when the user is editing the contours. The concept and functionality of a Virtual Touchpad is well known, for example, from U.S. Pat. No. 8,754,855 B2, which is incorporated by reference herein for all purposes. The virtual touchpad in the present disclosure has a different (specific) behavior, which will be explained further in Virtual Touchpad related sections. Button B does not have special definition for this group, and can be hidden or removed. Finally, for the Button A group, which is also just one Edit button with two states for Editing and not Editing. The Button A has been defined to have a special function to accept the edited contour result and update it back to the original contour. Without this action, the contour editing result is still displayed as a temporary object and maybe discarded when an Editing mode is terminated or stopped.

As used herein, Control Points and Anchor Points are defined as follows. Control points 402 are individual points on the algorithm-generated lumen contour 400 that represent a segment of the lumen contour 400 that substantially matches the true lumen edge 322 of the underlying tomographic image 321. Control points are automatically added by the algorithm that initially generates the lumen contour 400. Control points can also be added and/or removed by the user by simply touching or clicking on the curve of lumen contour 400. Non-matching control points 402 are individual points along the lumen contour 400 that represent a segment of the lumen contour 400 that does not match the true lumen edge 322 of the tomographic image 321. Non-matching contour points 402 are draggable control points (control points that can be dragged in one or more directions), which the user can move to alter the lumen contour 400 so that it matches with the true lumen edge 322 of the tomographic image 321. Anchor points 405 are special control points. As the name indicates, anchor points are anchored points that have a fixed location, which means the user cannot drag an anchor point to modify the curve of the lumen contour. While a control point 402 can be dragged to change the shape of the lumen contour, an anchor point 405 can be selected (to make it active), but it cannot be dragged.

The use of anchor points is particularly useful in editing modes B and C, where the user can draw a contour segment between two anchor points. Anchor points 405 can be connected by a drawn segment to change the contour shape. Anchor points can be distinguished from control points on the screen by using different colors and/or shapes. For example, when the lumen contour 400 is in yellow or orange color, the control points can be green circles, and the anchor points can be light-blue triangles (or stars as in FIG. 6A). The anchor points and control points can also convert to each other by double-click or hard-pressing on them. To remove anchor or control points, the user can draw an "X" on it, which means to delete the given point. As shown in FIG. 3, the editing tool provides a pre-defined "Clear All Control Points" button 507, which can be used to remove all control points for easy clean up. Moreover, the undo button 510 and redo button 511 can be used to add and remove individually added control points, or a multitude of control points added via the pulldown button 508.

Figure 4:
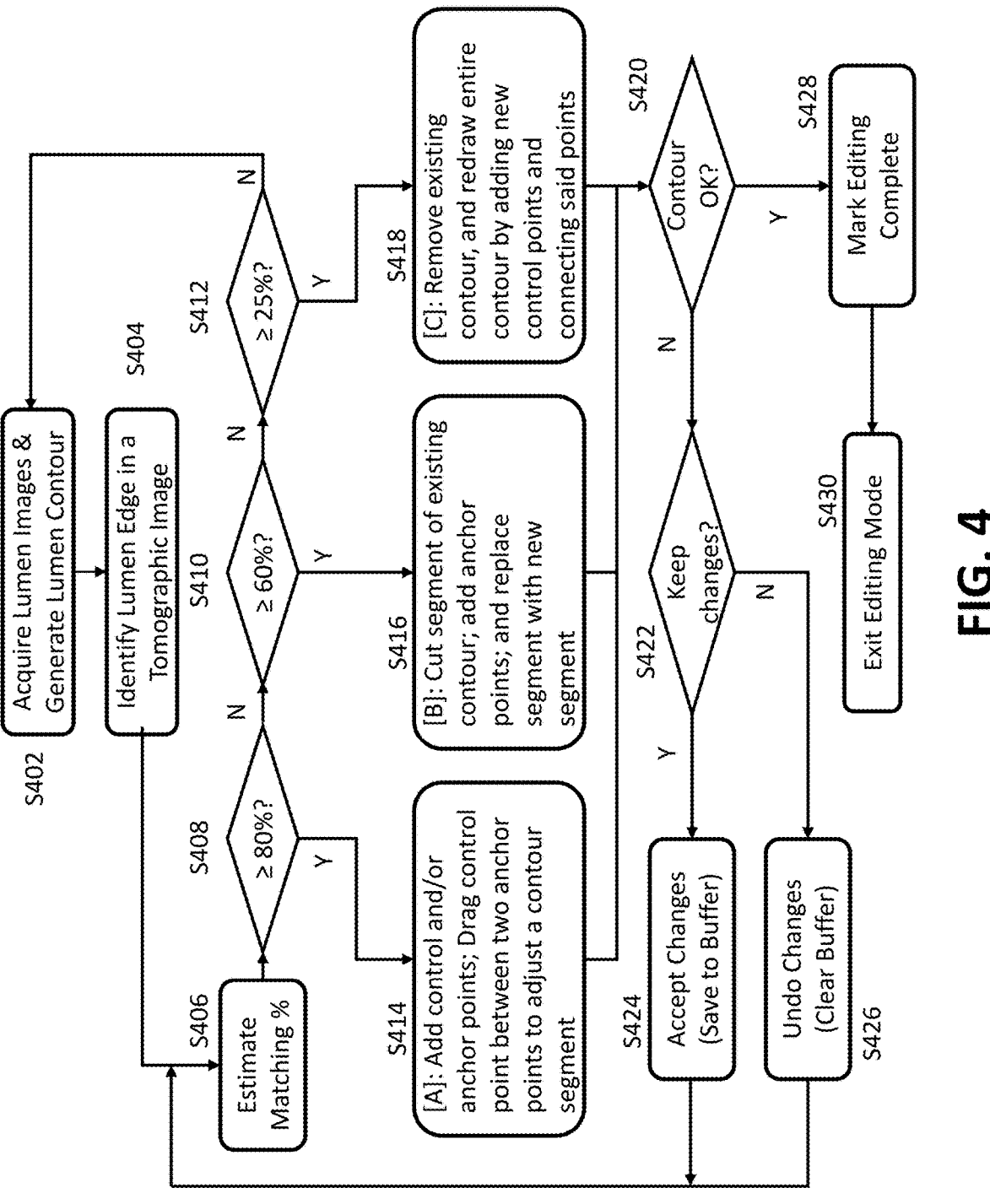
FIG. 4 is a flowchart illustrating an exemplary process (method/algorithm) for blood vessel identification and lumen contour editing, according to an embodiment of the present disclosure.

FIG. 4 is a flowchart illustrating an exemplary process (method) for blood vessel identification and lumen contour editing, according to an embodiment of the present disclosure. Operations or processes shown in FIG. 4 are implemented by the processor 210 of computer 200. Even in processes specifically described as being performed by the user, the processor 210 controls the editing process based on inputs from the user. At step S402, the system 100 acquires a plurality of images associated with vessel 170. Each of the plurality of images is preferably obtained at different locations of the vessel 170, or at different times or orientations within the vessel. In at least some embodiments, the plurality of images includes OCT data and fluorescence data obtained simultaneously along a length of the vessel. Upon receiving the plurality of images, the system executes one or more algorithms to create two-dimensional and/or three-dimensional images of the vessel.

Referring back to FIG. 2A, GUI 300 displays an OCT vessel image 331, a fluorescence carpet view 332, and a current OCT tomographic image 321 from a series of successive tomographic images of the OCT vessel image 331. Visible in the tomographic image 321 is a vessel lumen (the true lumen edge 322). An automatically computed vessel lumen contour 400 is also shown overlaid on top of the tomographic image 321. The automatically computed lumen contour 400 is generated based on well-known lumen detection algorithms. See for example, U.S. Pat. No. 11,382, 516 B2 ("LUMEN, STENT, AND/OR ARTIFACT DETECTION IN ONE OR MORE IMAGES, SUCH AS IN OPTICAL COHERENCE TOMOGRAPHY IMAGES") previously disclosed by the applicant of the present application, which is hereby incorporated by reference for all purposes.

The lumen contour 400 may be used, for example, in computing important parameters such as lumen diameter or lumen cross-sectional area, existence of plaque, etc., which may be critical in making clinical decisions such as stent sizing for treatment of one or more conditions of the patient. Therefore, it is important that the automatically computed lumen contour 400 is accurately defined. However, automatically generating the lumen contour 400 of the vessel becomes difficult due to several sources of ambiguity. For example, in a case where the vessel has side branches, the computed lumen contour 400 can be incomplete. Also, irregularly shaped vessel geometries, occlusions, compressions, stenosis, and stents, including sub-optimally placed or sub-optimally expanded stents can cause the automatically computed lumen contour 400 to not match with the true lumen edge 322.

Therefore, at step S404, the system may identify the true lumen edge 322 in the tomographic image 321. An example of identifying the true lumen edge of a blood vessel is described in pre-grant patent application publication US 2021/0407098 also disclosed by the same applicant of the present disclosure. After the true lumen edge 322 is identified, the user or the system can evaluate, compare, calculate, or estimate an amount of matching between the true lumen edge 322 and the automatically-generated lumen contour 400.

Specifically, the user may choose to enter Editing Mode. Choosing to enter editing mode can include, for example, choosing one or more of editing tools 325A-532D from tool-selecting section 352. Alternatively, the system may actively prompt the user to enter the editing mode.

Once the user has chosen to enter the editing mode, the system analyzes the current tomographic image and the automatically-generated lumen contour 400 to assist the user in more efficiently matching the lumen contour 400 to the true lumen edge 322 of the tomographic image 321. To that end, at step S406, the system determines a percentage of matching between the true lumen edge 322 of the tomographic image and the automatically generated lumen contour 400. At step s408, the system determines if the auto generated contour 400 matches at least 80% of the true lumen edge 322. Here, the determination can be based on statistical comparisons using, for example, machine learning algorithms. In some embodiments, the comparison between the automatically generated lumen contour 400 and the true lumen edge 322 employs a machine learning network (e.g., a learning artificial neuron network (ANN) with multiple layers between the input and output layers), trained on sets of comparable OCT image data using previously identified lumen borders. The percentage of matching is a metric defined using a full circle or ellipse of the lumen contour as the 100% and comparing sample points from two different sources and apply an empirical determined threshold to mark the matching vs no-matching edge point samples evenly distributed around the contour. An example of this process was described by L. Athanasiou et al., "Optimized Computer Aided Segmentation and Three-Dimensional Reconstruction Using Intracoronary Optical Coherence Tomography," in IEEE Journal of Biomedical and Health Informatics, vol. 22, no. 4, pp. 1168-1176, July 2018, doi: 10.1109/JBHI.2017.2762520. If the matching between automatically generated lumen contour 400 and the true lumen edge 322 is equal to or greater than 80% (YES at S408), the process advances to step S414.

If the matching determination at S408 is less than 80% (NO at S408), the process advances to step S410. At step S410, the system determines if matching is equal to or greater than 60%. If the matching determination at S410 is equal to or greater than 60% (YES at S410), the process advances to step S416. If the matching determination at S410 is less than 60% (NO at S406), the process advances to step S412. At step S412, the system determines if matching is equal to or greater than 25%. If the matching determination at S412 is equal to or greater than 25% (YES at S412), the process advances to step S418. If the matching determination at S412 is less than 25% (NO at S412), the process returns to step S402. Specifically, at step S412, if the automatically generated lumen contour 400 does not match at least 25% of the true lumen edge 322 of the tomographic image 321, there is a high possibility that either the acquired image 321 or the automatically generated lumen contour 400 are incomplete or include some other major error. For this reason, the system returns to step S402, where the system acquires a new tomographic image of the lumen, and automatically generates a lumen contour 400 for the new image. Here, it should be noted that the percentage of matching in S408, S410, and S412 are merely examples. These values can be changed according to the system needs or user preference. However, it is important to recognize that the different values allow the system to provide a plurality of editing modes in which the automatically generated lumen contour 400 can be edited incrementally from only a small portion of the contour under mode A, a segment of the contour under mode B, or replacing the entire lumen contour under mode C.

More specifically, at step S414, the system enables a first editing mode (mode A). In mode A, since the automatically generated lumen contour 40o already matches at least 80% of the true lumen edge 322 in the tomographic image 321, the user can edit only the part (e.g., a small segment between two or more control points) of contour 40o that does not match the true lumen edge 322. To that end, the user can manually add control points and/or anchor points to the segment of the image that does not match the automatically generated lumen contour. The user can also drag a control point between two anchor points to adjust the contour segment. Here, to implement the editing mode A, the user may use a predefined editing tool 352, which allows the user to edit a short segment between two control points. After the appropriate adjustments are made at step S414, the process advances to step S420.

At step S416, the system enables a second editing mode (mode B). In mode B, since the automatically generated lumen contour matches only the 60% of the image, the user can edit the segment of contour 400 that does not match the true lumen edge 322. To that end, the user can manually "cut" the segment that does not match, add control points and/or anchor points along the lumen edge of the tomographic image that does not match the automatically generated lumen contour 400. The user or the system can connect the newly added points by drawing a new lumen contour segment along the true lumen edge of the image. To implement fine adjustments of the newly drawn contour line, the user can also drag a control point between each pair of anchor points to adjust the newly drawn contour segment. After the appropriate adjustments are made at step S414, the process advances to step S420.

At step S418, the system enables a third editing mode (mode C). In mode C, since the automatically generated lumen contour matches only the 25% of the image, the user can edit the segment of contour that does not match. To that end, the user can manually "remove" (delete) the entire contour, and manually redraw a new contour. That is, since the automatically generated lumen contour matches only the 25% of the image, it is better to replace the entire lumen contour. To that end, the user can add new control points around the lumen edge in the image. Then, the system can connect the control points to generate a new lumen contour. To implement fine adjustment of the newly drawn lumen contour, the user can designate certain control points as anchor points. For example, double pressing or pressing for a relatively long period (e.g., 2 or more seconds) can convert a control point into an anchor point. Thereafter, the user can drag a control point between each pair of anchor points to finely adjust the lumen contour until it matches the image. After the appropriate adjustments are made at step S418, the process advances to step S420.

At step S420, the system again provides an additional opportunity to the user to confirm whether the recently edited contour is acceptable. At step S420, if the user decides that the newly edited contour is not acceptable, the process advances to step S422. At step S422, the system prompts the user whether to keep the changes already made to the lumen contour. If the user decides to keep the changes, the process advances to step S424. At step S424, the system saves the changes to the memory buffer. If the user decides to not keep the changes, the process advances to step S426. At step S426, the system clears the memory buffer, thereby undoing all changes made in the previous processes. From step S424 and/or step S426, the process returns to step S406. At step S406, the system will use the changes saved in the memory buffer at step S424 to again determine the percentage of matching of the edited lumen contour to the original image. It is assumed that, when the system returns to step s406 after saving the changes already made, then matching percentage should increase with each iteration, until the edited lumen contour becomes acceptable, and the system exits the editing mode.

More specifically, if the user accepts the edited contour (YES at S420), the flow proceeds to step S428. At step S428, the user can mark the editing process as complete. Thereafter, at step S430, the system exits the contour editing mode.

Figure 5A:
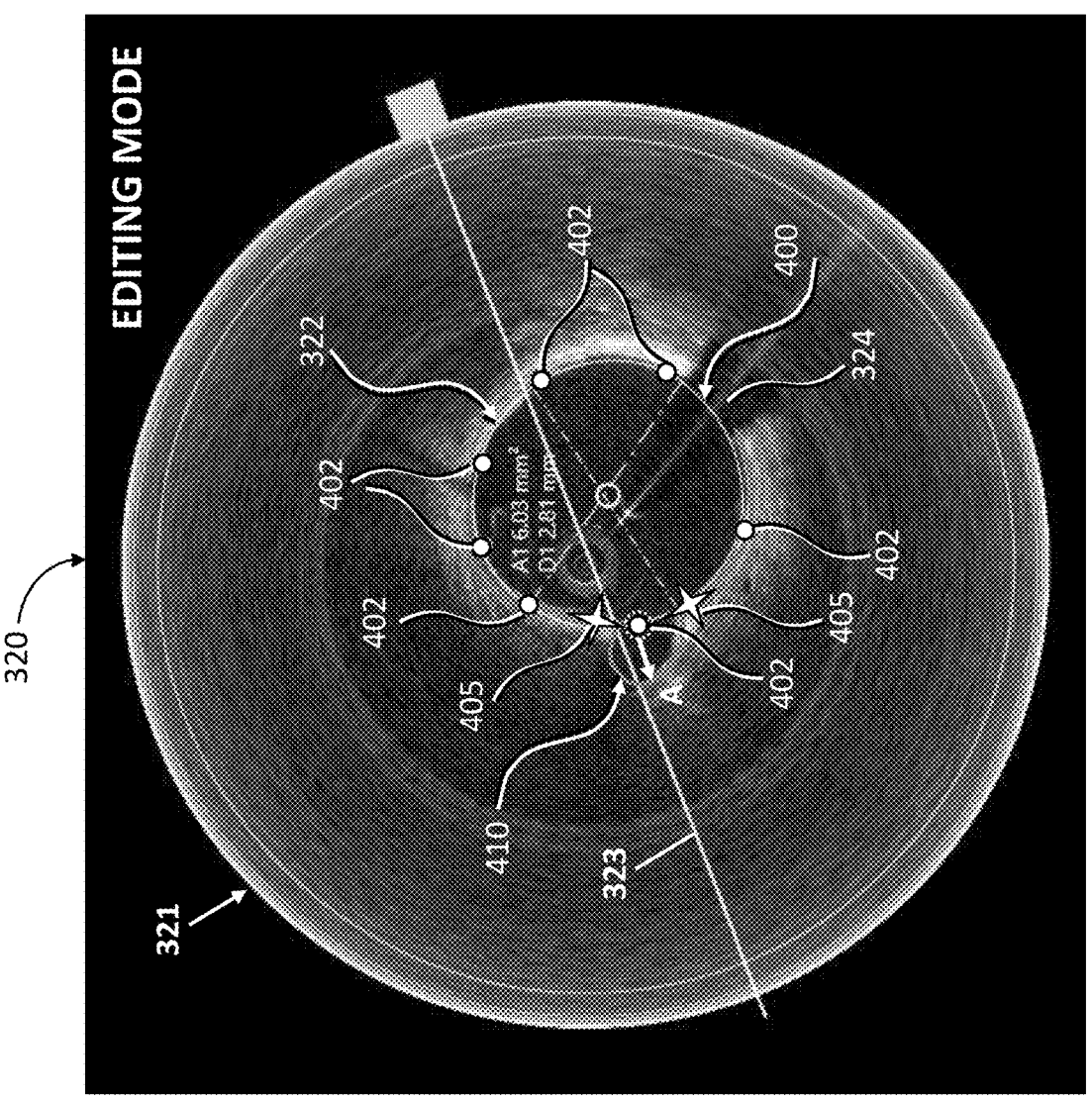
FIG. 5A and FIG. 5B illustrate examples of lumen contour editing of a tomographic image of a vessel to obtain an edited lumen contour.
Figure 5B:
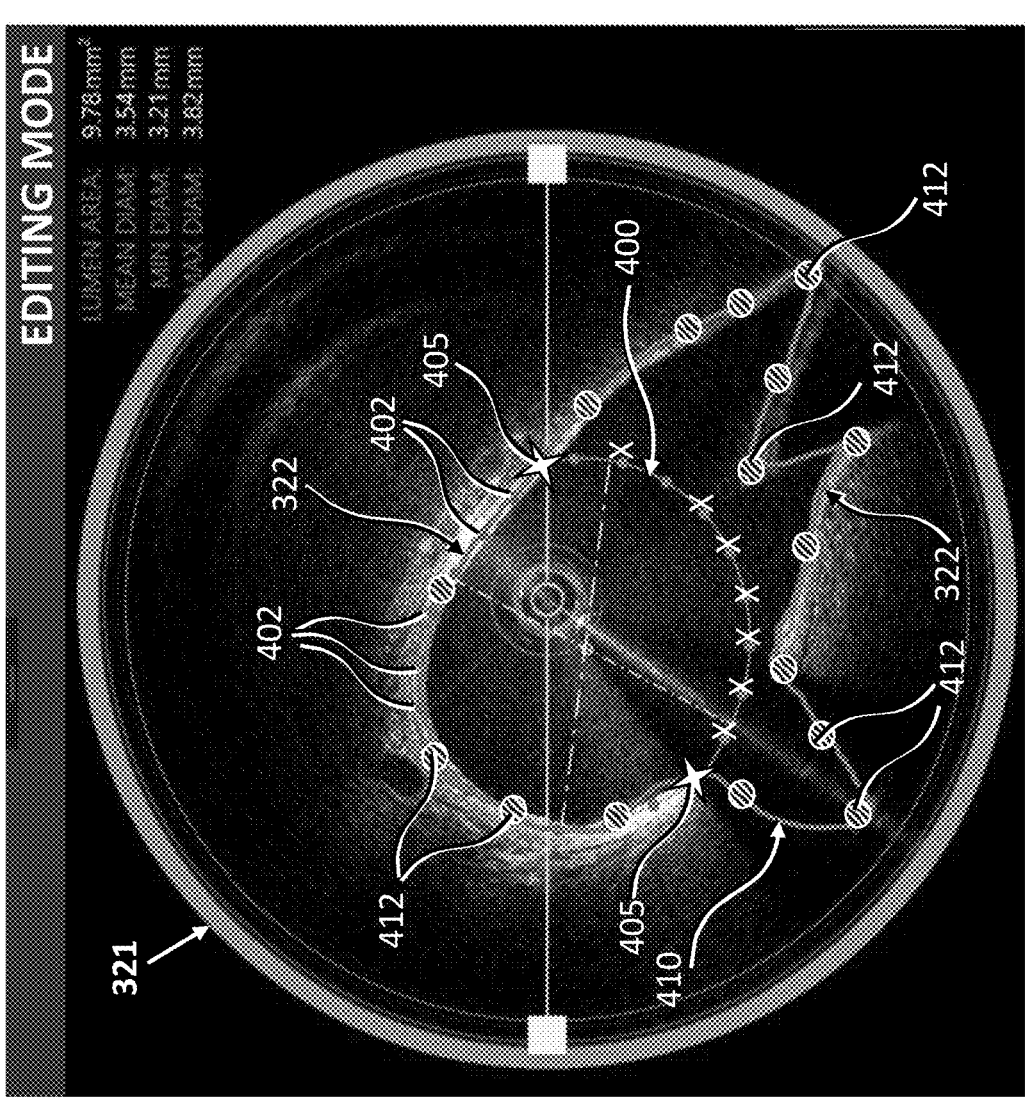

FIG. 5A and FIG. 5B illustrate examples of contour editing as described above. In FIG. 5A and FIG. 5B, an automatically generated lumen contour 400 is displayed on top the tomographic image 321. When the contour 400 does not match with the actual edge 322 of the MMOCT image underneath, the present disclosure provides an interactive touchscreen tool that allows the user to make corrections freely with few steps. More specifically, it is well known that in a sterile environments of the medical field, it is impractical and difficult to use a pointer device such as a computer mouse to control imaging operations. According to at least one embodiment of the present disclosure, it is advantageous to display the lumen contour 400 in a manner that can facilitate editing operations by a user using a simple editing tool to reshape the contour (curve) of the automatically-generated lumen contour 400. For example, after the user recognizes that the automatically generated lumen contour 400 does not accurately match the true lumen edge of the tomographic image with at least an 80% of accuracy. The editing tool section 351 provides a plurality of predefined tools to help the user quickly reach the appropriate lumen contour shape based on a determination of an amount (or percentage) of matching between the lumen edge in the tomographic view and the algorithm-generated lumen contour 400. To that end, as shown in the remainder examples of this disclosure, the user can use a touchscreen to individually adjust certain points or segments of the lumen contour 400 to manually match the true lumen edge 322. Alternatively, when the mismatch is too large (i.e., matching is less than 25%), the user can quickly replace the entire computer-generated lumen contour 400 for a manually drawn one.

In FIG. 5A, the algorithm-generated lumen contour 400 is displayed with a plurality of "control points" 402. The control points 402 that substantially match the true lumen edge 322 of the tomographic image 321 are referred to a matching control points 402, and the control points that don't match with the true lumen edge 322 are called non-matching control points 402. In FIG. 5A, there is a region 324 corresponding to an artifact created by the catheter 160 (or a guidewire); in the region 324, the lumen edge 322 is not shown. In addition, in the tomographic image 321 there is a region 325 where the lumen edge 322 does not match the algorithm-generated lumen contour 400. In this case, to be able to accurately determine the area (or diameter) of the lumen, the lumen contour 400 must be adjusted by moving a non-matching control point 402 in a direction of arrow A until the lumen contour 40o matches the true lumen edge 322. In this case, the user can designate some control points as anchor points 405. Anchor points can be designated by the user by tapping or holding on the corresponding point/ location of the lumen contour 400. Anchor points fix the lumen contour 400 to the edge of the lumen shown in the tomographic image. After the two anchor points 405 are designated, the user can drag the control point 402 in direction of arrow A until an edited lumen contour 410 matches the true lumen edge 322 of the tomographic image 321. This is an example of editing under Mode A shown in FIG. 4.

In FIG. 5B, the algorithm generated lumen contour 400 is similarly displayed with matching control points 402 that substantially match only a portion of the lumen edge 322 of the tomographic image 321. However, a larger portion of non-matching control points 402 are relatively far from the true lumen edge 322 of the tomographic image 321. In this case, instead of trying to edit the lumen contour 40o by dragging each of the non-matching control points 402, the user can cut and replace a section of the lumen contour 400, or the user can delete (remove) the entire computer-generated lumen contour 400, and manually replace the contour 400 with a new lumen contour 410. To that end, the user can first delete the non-matching segments by pressing on each non-matching control point 402. In FIG. 5B, an "x" on the control points 402 represents the deleting of at least a segment of the computer-generated lumen contour 400. Subsequently, the user adds new control points 412 by touching on the true lumen edge 322 of the tomographic image 321. After the control points 412 are added, the user can manually connect the control points 412, by drawing a line to connect the added control points 412. Alternatively, the computer can be programmed to automatically connect the newly added control points 412, e.g., by splines between two or more of the new control points 412. In this case too, to make fine adjustments, the user can designate some of the new control points 412 as anchor points having at least one control point in between. Thereafter, the user can drag the control point in any direction until the new lumen boundary 410 matches the true lumen edge 322 of the tomographic image 321, as best as possible. This process is an example of contour editing under Mode B or Mode C illustrated in FIG. 4.

In other words, once the system enters the editing mode, the user can interactively drag the non-matching control points 402 radially away from the center of lumen, or move the non-matching control points 402 radially towards the center of the lumen to match the computer-generated contour 400 with the true lumen edge 322, as explained above according to mode A. Notably, for severely irregular vessel walls as shown in FIG. 5B, for example, the user can remove part (a segment) or the entirety of the automatically generated lumen contour 400, and manually add a new lumen boundary 410 by manually placing new control points 412 and connecting the new control points 412 to replace the removed part or entire lumen contour 400, explained above according to modes B and C. Once the user is satisfied with the manual editing process, the user can input a confirmation that the editing is acceptable so that the system can accept the changes made.

Example 1

Figure 6A:
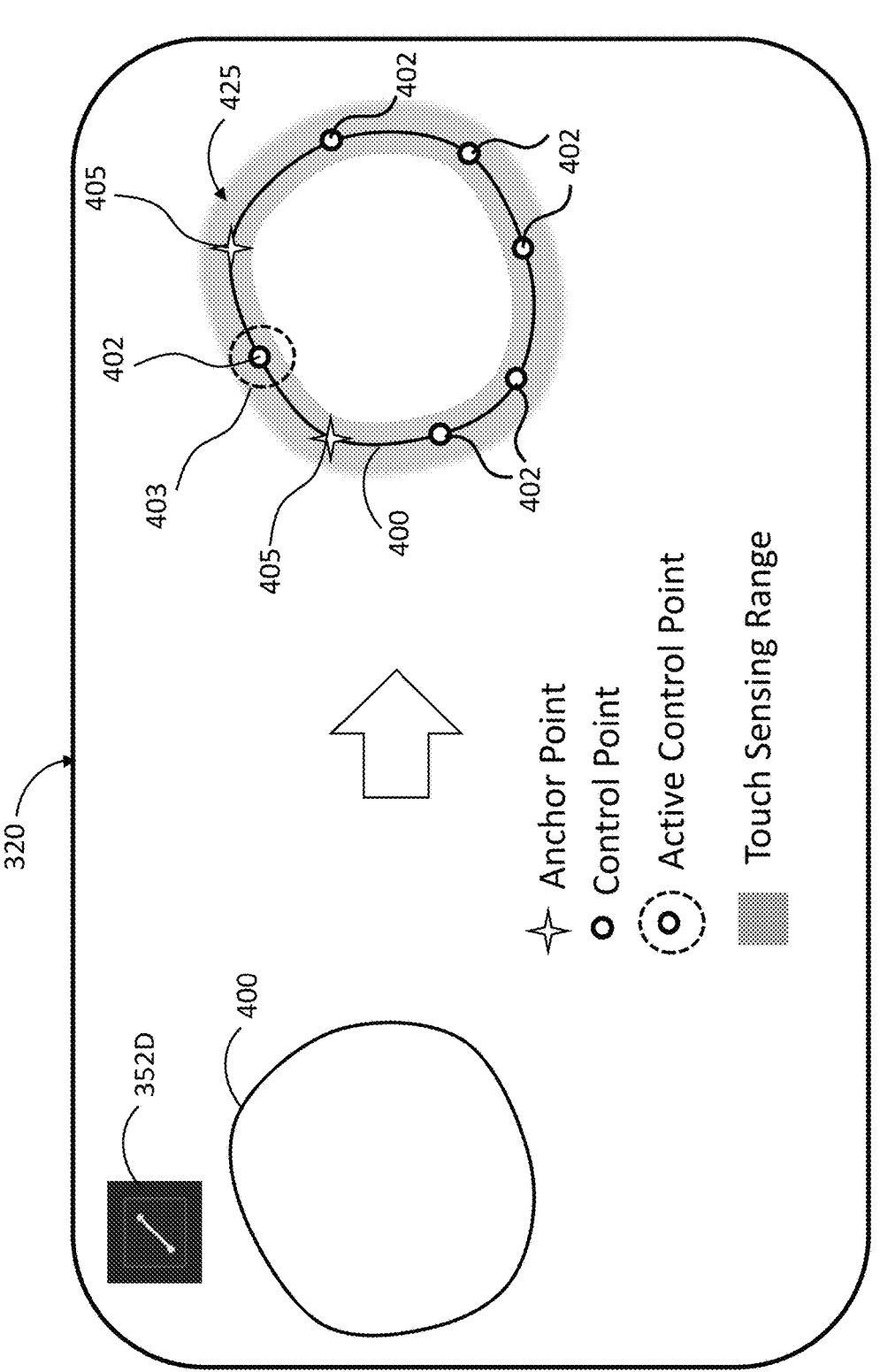
FIG. 6A and FIG. 6B illustrates an example of lumen contour editing using a touchscreen user interface, according to a first editing mode.

FIG. 6A illustrates an example of the contour editing according to "Mode A". In this example, the automatically generated lumen contour 400 is edited to better match the true lumen edge 322 of the tomographic image 321 by manipulating one or more control points. Under contour editing mode A, the contour editing tool allows the user to manipulate one or more control points one at a time. To move a control point, two anchor points (one on each side of the control point) are preferred, so that only a contour segment between two anchor points can be altered. In this mode, there are following assumptions specific to this approach: 1) multiple control points may exist on the lumen contour 400 to separate it into segments; 2) when a control point is dragged, the two neighbor control points are fixed in location; the control points fixed in location are named "anchor points"; 3) if a spot of the contour needs to be dragged but such spot is not yet a control point, a draggable control point is added at the desired spot; 4) dragging a control point selected with Ctrl key down will move the contour segment to follow the spline interpolated between two neighboring anchor points. In computer graphics, a spline is a curve that connects two or more specific points, or a curve that is defined by two or more points. The term spline can also refer to the mathematical equation that defines such a curve. Cubic spline interpolation is a mathematical method commonly used to construct new points within the boundaries of a set of known control points. There are numerous type of spline interpolation, hence, the result of interpolation may vary depending on different type of splines used. As an example, B-spline (or basic spline) is chosen as a way to calculate the cubic spline interpolation while also giving control points localized control. Therefore, B-spline is a good example of spline implementation.

According to FIG. 6A, the display section 320 of GUI 300 initially shows only the lumen contour 400 without the underlying tomographic image 321. After the lumen contour 400 is shown, the user can choose one of editing tools 352A, 352B, 352C or 352D from editing tool-selecting section 352. Each of these tools can be predefined based on specific spline interpolation types already programmed in computer 200. Once the user choses a contour editing tool from the contour editing tool-selecting section 352, the lumen contour 400 will be displayed on the OCT Tomo Viewer with some overlay objects. Specifically, the true lumen edge 322 of the OCT image 321 will be shown first; then, the automatically generated lumen contour 400 is displayed with a shadow band 245 superposed with the lumen contour 400. Control points (dots) 402 are added automatically by the system based on the algorithm used to generate the lumen contour 400. The number of control points 402 depends, among other things, on the shape and size of the lumen contour 400. By observing this image, the user can determine the region or portion of the lumen contour 400 that needs to be altered to match with the true lumen edge 322 of the tomographic image. To manipulate a portion of the lumen contour 400, anchor points 405 (stars) can be added by the user on top of the lumen contour 400. Anchor points 405 can be additional points added by the user at desired locations, or can be original control points 402 converted into anchor points by the user selecting and holding a control point for a predetermined amount of time (for example, holding a control point for a few seconds causes the computer 200 to change a control point 402 into an anchor point 405). The control point 402 between two anchor points becomes a drag able control point 402. More than one control point can exist between two anchor points. An active or selected control point 402 that is ready to be dragged can be shown with an active indicator 403 (see FIG. 6A).

Figure 6B:
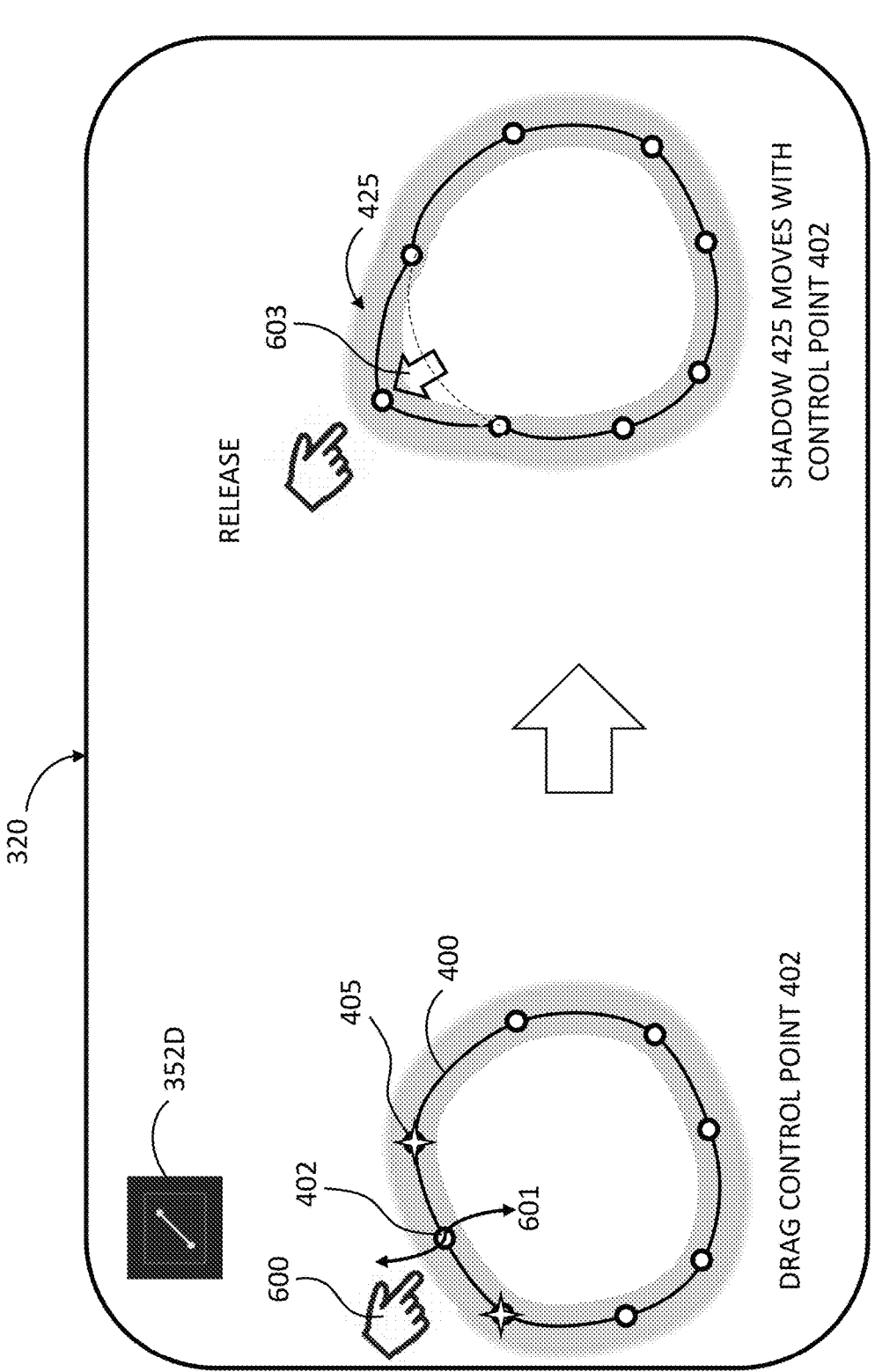

FIG. 6B shows an example of the user's hand 600 (an icon of the user's hand) acting on a control point 402. Here, the icon of the user's hand 600 represents the actual physical hand (or one or more fingers) of the user interacting with the touchscreen of the graphical user interface. The user's finger can drag (pull) the control point 402 away from the center of the tomographic image, or it can push the control point 402 towards the center of the tomographic image. The user's dragging movement shown by arrow 601 will change the shape of lumen contour 400 according to the effected movement to eventually match the true lumen edge 322 of the tomographic image 321. In this case, under editing Mode A, only the segments between two neighboring anchor points 405 are changed according to the directions in which the control point 402 is moved. The user can choose the location of the anchor points 405 on the lumen contour 400 by, e.g., tapping multiple times (e.g., two or more times) on a location along the curve of contour 400, or holding down the Ctrl key on the keyboard (not shown) and clicking or touching on the desired location, before dragging the control point 402. The shadow band 425 moves together with the control point 402 and the portion of the lumen contour 400 that is being edited. When the user releases the control point 402, the shadow band 425 and the lumen contour 40*o* are also released (stop moving).

The manner in which a control point is moved by the user is not limited to the described examples. In other embodiments, the algorithm-generated lumen contour 400 can be reshaped without consideration for already existing control points. For example, without selecting a control point, the user can select an arbitrary spot (point) on the lumen contour 400 and "pull" or "push" the selected spot along with a portion of the contour 400 on either side of the spot to a desired location so as to cause the contour 400 to match the true lumen edge 322 of the tomographic image 321. This is similar to the example shown in FIG. 5B. In this case, the system can be programmed to limit the length of the portion of the contour 400 on either side of the arbitrarily selected spot that can be moved when the user pulls or pushes the selected spot. The user can also select two or more arbitrary points on the contour 400 to modify, delete or replace certain sections of the lumen contour 400. These processes can be similar to the "reshaping of paths without respect to control points" described in U.S. Pat. No. 6,459,439, which is hereby incorporated by reference as if fully set forth herein.

Figure 7:
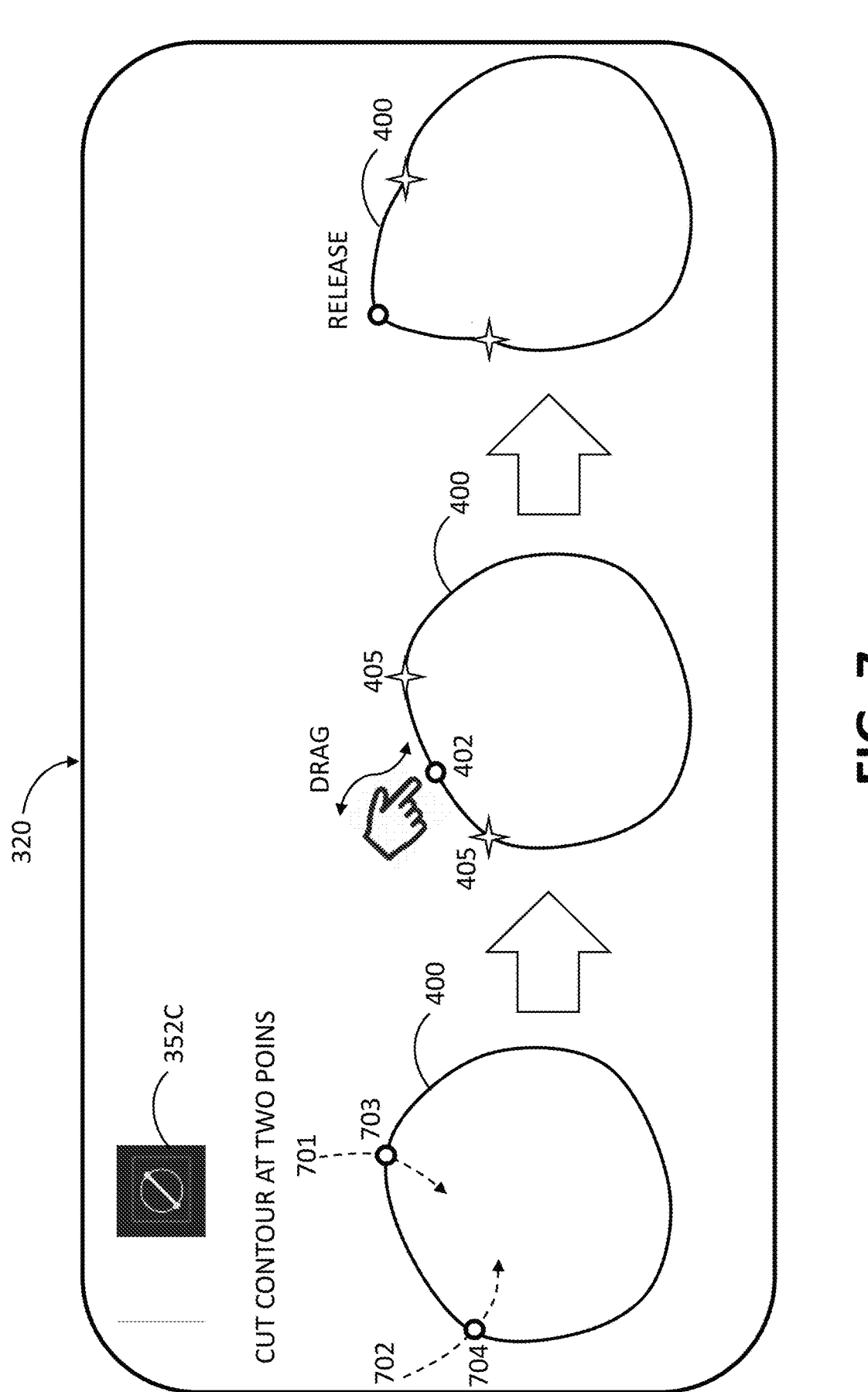
FIG. 7 shows an example of a manner in which a user can define one or more anchor points 405 and add a control point 402 using a touchscreen user interface to adjust or modify a segment of a lumen contour 400.

FIG. 7 shows another example of a manner in which a user can define one or more anchor points to modify the lumen contour 400. According to FIG. 7, the user can draw one or more lines 701, 702 (straight or curved lines) that will intersect with lumen contour 400 from outside to inside. The user draws a first line 701 which intersects contour lumen 400 at a first point 703, and a second line 702 which intersects the lumen contour 400 at a second point 704. The first point 703 and second point 704 where the one or more lines intersect the lumen contour 400 become anchor points 405. Then, the user can select and arbitrary spot between two anchor points to apply a dragging action similar to those described above to alter the segment of lumen contour 400 defined between two anchor points. The spot chosen by user between the anchor points can be an arbitrary point, or can it be the middle distance along the segment of lumen contour 400, and such spot becomes a control point 402 to be dragged by the user according to the desired needs. In FIG.

7, for example, the user drags the new control point 402 towards the outside (radially away) from the center of the tomographic image. Once the lumen contour 400 is adjusted as needed, the user releases the control point to thereby complete the editing operation.

FIG. 6A, FIG. 6B and FIG. 7 are examples of contour editing under Mode A. When using this mode, the contour editing tool will reach reasonably good results when the expected results are following the spline curve shape. Meanwhile, the contour curve beyond two anchor points defined segments should be kept as is without any change. The original contour's curvatures on two anchor points are also preserved and will be used to determine the ideal shape of the interpolated spline.

Example 2

Figure 8:
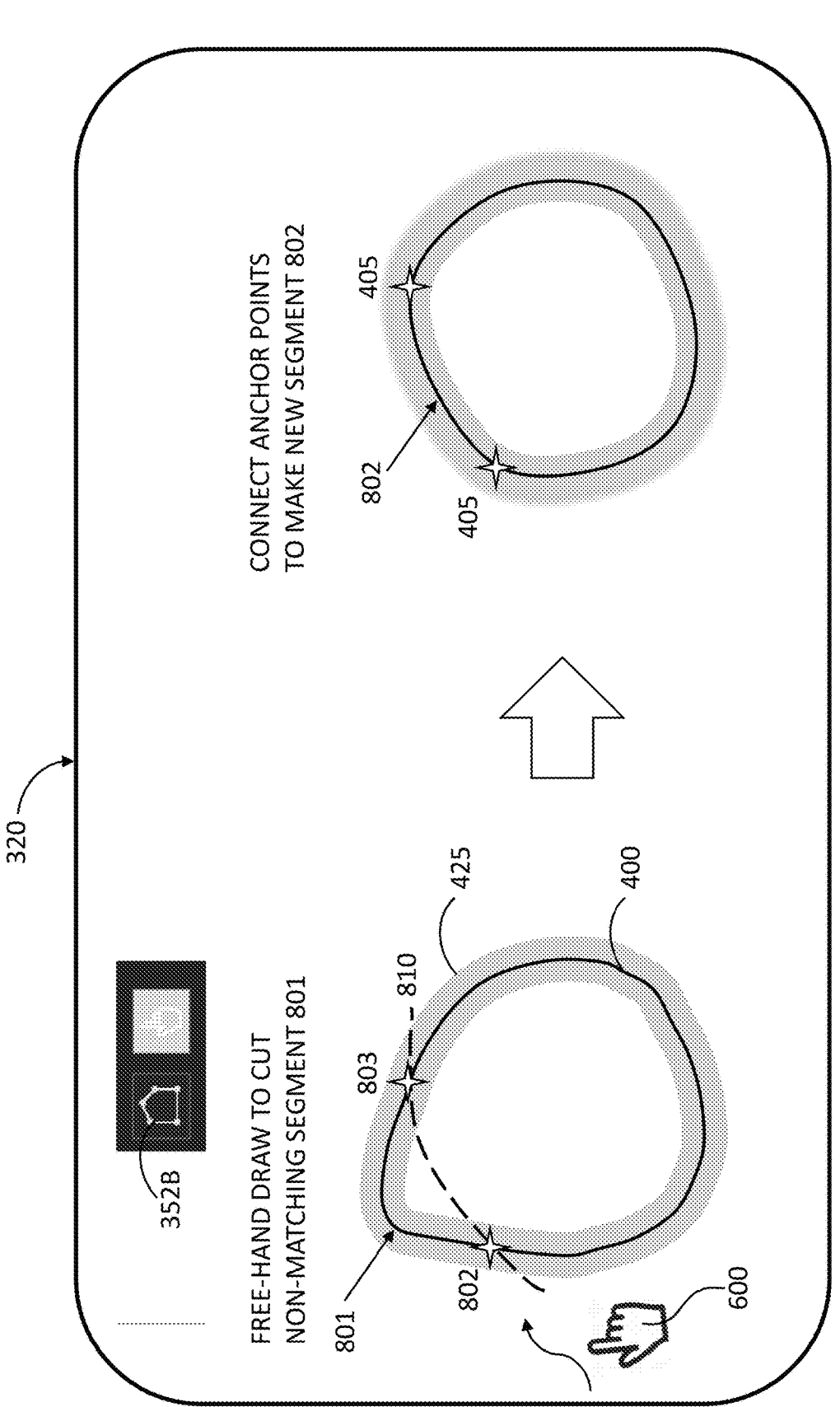
FIG. 8 illustrates an example of lumen contour editing in which a user can cut (delete) a segment of a lumen contour 400 and replace with a new segment 802, using a touchscreen user interface to adjust a lumen contour 400, according to a second editing mode.

FIG. 8 shows an example of contour editing under Mode B. Under contour editing Mode B, the user can redraw a segment of the algorithm-generated lumen contour 400. According to Mode B, the system is configured to consider the finger touch or mouse drag movement as a pen drawing on a surface. A user can draw a segment from one point on existing contour to another point on the contour and replace the segment in between. In order to distinguish from dragging a control point as in mode A, contour editing under mode B requires the start and end points of the drawing process to be away from the contour and to draw the segment cross the original contour exactly twice. In another words, both the start and end points will be inside the contour and the newly drawn curve is outside the contour, or both the start and end points will be outside the contour and the newly drawn curve is inside the contour. Then the original contour's segment between two intersection points is replaced by a newly drawn curve.

According to FIG. 8, under contour editing mode B, a user can directly redraw a segment 801 of contour 400 using free-hand drawing. No predefined control points or anchor points are necessary. The user simply draws a line 810 that intersects with the lumen contour 400 at a first point 802 and as second point 803. The system then removes the segment 801 of the contour 400 that is outside of these two points; converts the two points 802-803 into anchor points 405, and automatically connects the remaining contour 400 to the segment of line 810 drawn by the user. The segment of line 810 will be kept as new segment 802 that replaces the original shape of the contour 400. After the system connects the segment 802 of line 810 to the original contour 400, the two intersection points 802-803 automatically become anchor points 405. Then the user can make finer adjustments by dragging the new segment 802 in a desired direction so that the lumen contour 400 matches the true lumen edge 322.

Another alternative of editing under mode B is that if two anchor points are defined ahead of time, then the drawing can happen from one anchor point to another, and the original segment of contour 400 between the two anchor points will be deleted and replaced by the newly drawn segment.

Figure 9:
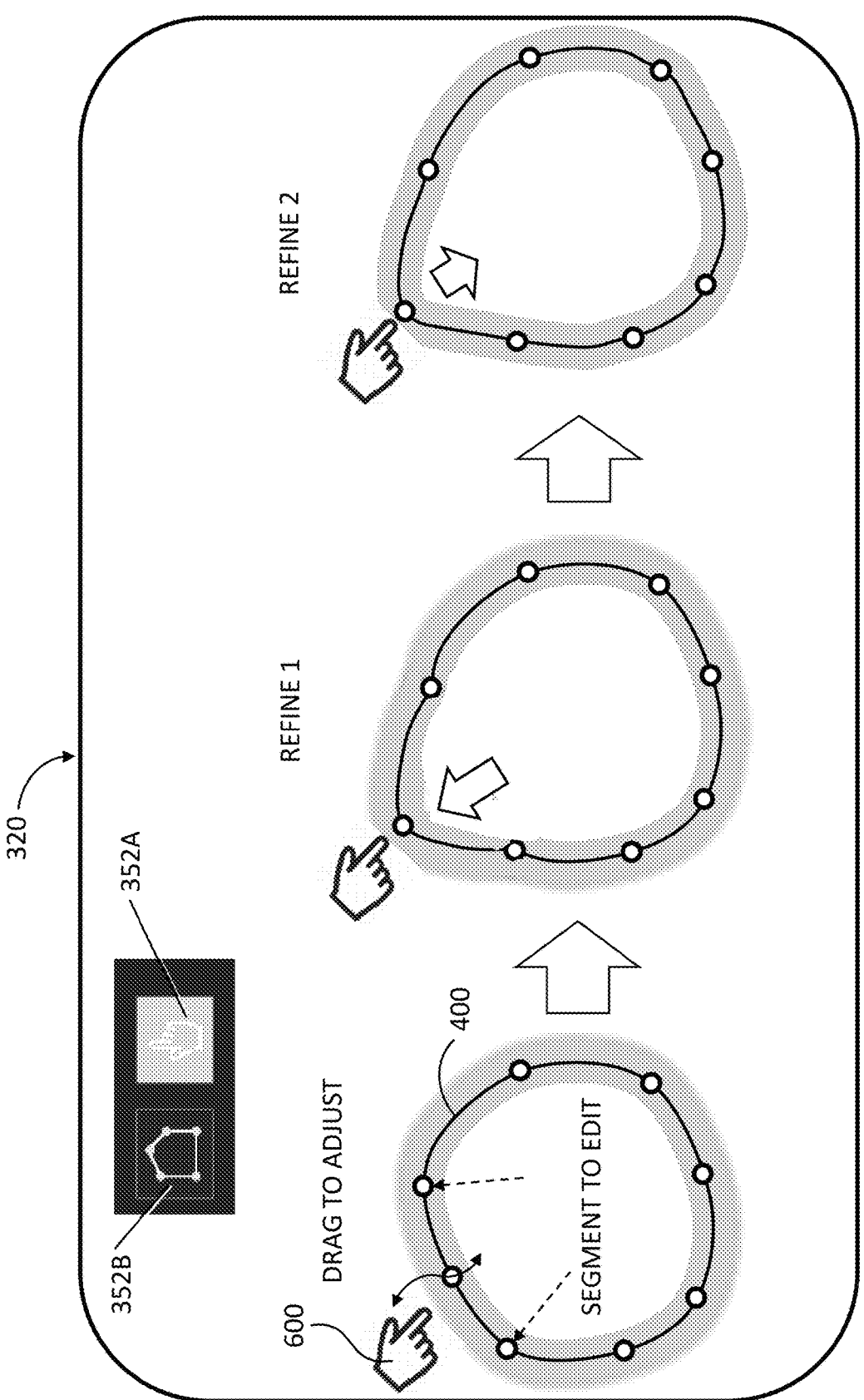
FIG. 9 illustrates an example of lumen contour editing in which the user may redraw a lumen contour, add control points, and refine a shape of the lumen contour using a touchscreen interface according to Draw, Select, Drag operations via the touchscreen interface, according to a third editing method.

Due to the nature of freehand drawing over a curved lumen contour 400, the intersection of the drawn line with the curve of the lumen contour 400 may not be smoothly connected at the intersection points. Therefore, an adjustment of the drawn segment at the intersection points (which become anchor points) will be applied automatically (or manually) based on original curvature of the contour 400. This process is referred to as a "corner auto-smoothing step". FIG. 9 shows an example of the corner auto-smoothing step. First, the user applies freehand movement on the touchscreen to draw or drag a segment which is automatically connected to the original curve of the contour 400. Afterwards, the user can drag the newly drawn segment to alter and adjust to approximately match the true lumen edge 322. Finally, the system can refine the curve of contour 400 by automatically adjusting the connections (corner auto-smoothing). In the process of corner auto-smoothing, not only the newly formed connections, but also the original control points and/or anchor points can be automatically adjusted.

The result of contour editing under Mode B followed by the corner auto-smoothing step will best represent the segment drawn by the user and seemingly merge the newly drawn segment with the original lumen contour 400. If any discrepancy remains between the edited contour and the true lumen edge 322, the user may choose to either undo the newly drawn segment, or keep the newly drawn segment and use editing Mode A to further refine the results.

Example 3

Figure 10:
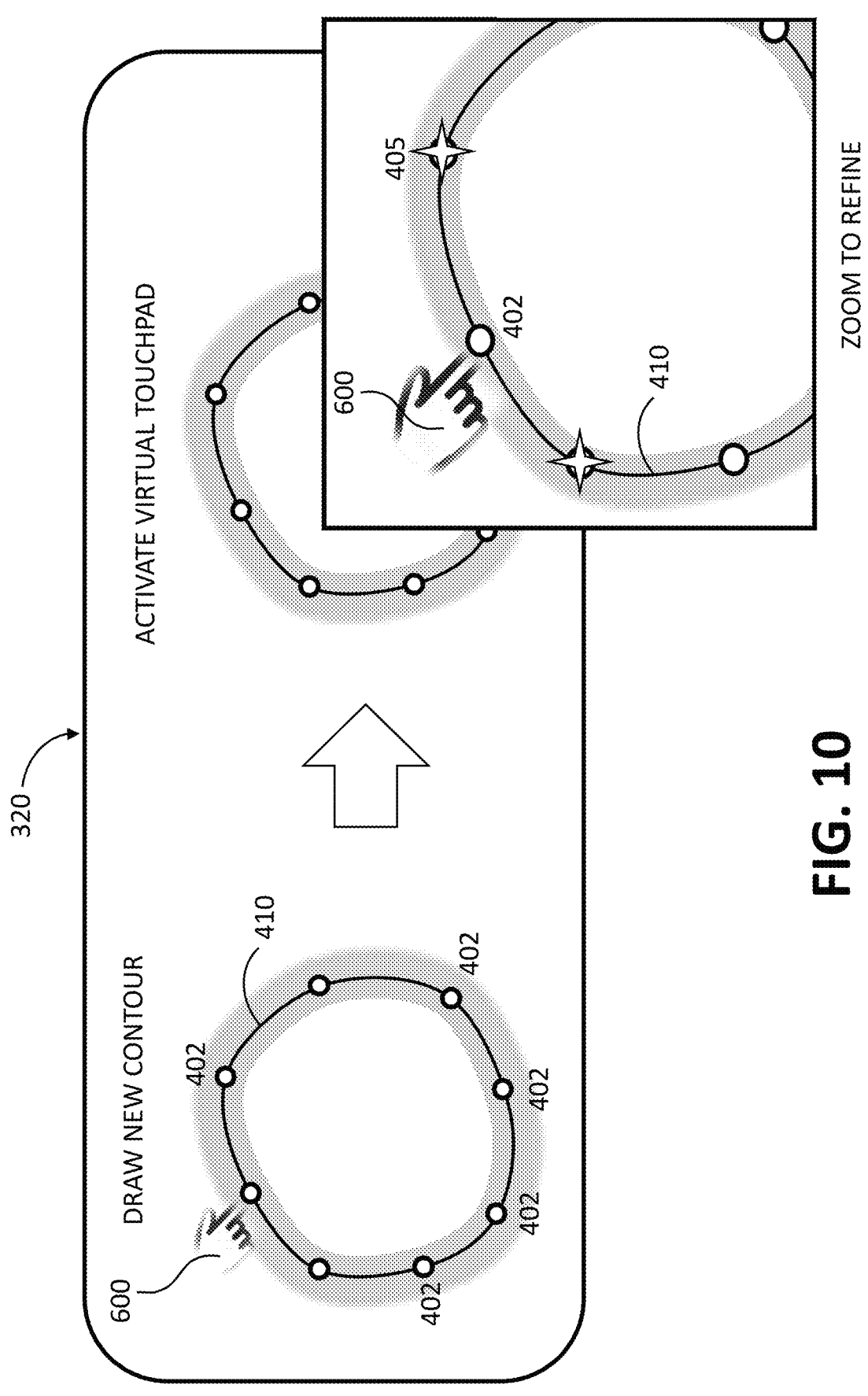
FIG. 10 illustrates an example of contour editing according to Drag or Draw touchscreen operations followed by one or more refining operations through the use of a virtual touchpad.

FIG. 10 illustrates an example of contour editing under Mode C. According to mode C the user can discard (delete) the algorithm-generated lumen contour 400 or a segment thereof, and replace it with control points arranged along the true lumen edge 322 of the tomographic image 321. Under mode C, at the beginning of the contour editing process, since the lumen contour 400 does not match at least 25% of the true lumen edge 322, the user can clear (delete) the whole contour 400. Then, the user redraws a new contour by first setting a plurality of points 402 around the true lumen edge 322. These points manually set by the user become control points for the desired contour. After setting the control points 402 for the new contour, the user can provide input to the system. Upon receiving such input, the system can automatically connect (auto connect) the control points, to thereby draw a new lumen contour 410. Because the system will connect all control points using spline curves, Mode C does not initially guarantee that the curvature of the newly drawn contour will accurately match the true lumen edge 322 of the underlying tomographic image. However, the newly drawn lumen contour 410 provides a good estimate with better matching than 25%. The newly drawn lumen contour 410 can then be used as a base for the other editing modes to do further refined adjustments.

Contour editing under mode C can be used for drawing the segment step, if the desired curve is similar to a spline curve. When user has already defined two anchor points, connecting these two points can use a few touches on the touchscreen (or can be done by a few clicks of the mouse). The user may first touch or click the start and end anchor points, and then click additional points outside the contour curve to add additional control points in sequence. The corresponding interpolated curve will be displayed instantly on each touch or click. During the process, the user may be unsatisfied with the position of a new control point. In that case, the user can use an undo a step to delete the last point added. In addition, the user can select any points previously added, and then drag and move them around like in mode A. After the user is satisfied with all the points and curve segments added, the user can input a command (e.g. by touching a button corresponding to "complete" step) to stop the editing process.

The foregoing examples have described different ways to edit the computer generated lumen contour 400. As mentioned above, in order for the different editing modes to be more effective, each mode can be combined with one or more other modes. In other words, the editing process can be implemented by iteratively following the editing process of FIG. 4 in which a different mode [A, B, or C] can be followed according to the degree (percentage) of matching. In that regard, it will be appreciated by those skilled in the art that, as the percentage of matching increases, the editing modes can be iterated from Mode C to Mode B to Mode A to improve (increase) percentage of matching between the true lumen edge 322 and the computer generated lumen contour 400. Next, some terminology used in this document specific to the present disclosure is defined with respect to contour editing. Based on the definitions and descriptions above, general usage steps and scenarios are applied to one or more editing examples used to demonstrate the workflow that uses the concepts of contour editing disclosed herein.
<Editing Accuracy>

To make the curve of lumen contour 400 easier to be touched on a touchscreen, a shadow band that functions as a touch sensing range 425 is defined in the system software along with the lumen contour 400. The touch sensing range can be defined as a function of screen resolution of display device 25o. The touch sensing range 425 can be displayed as a shadow band superposed or overlaid (over or under) the lumen contour 400. The size of the touch sensing range 425 (width of the shadow band) can be limited by the size of the lumen contour itself, and the shadow can be created by changing the color value of a certain number of pixels either outside, inside, or on both sides of the line defining the lumen contour 400. When lumen contour 400 is too small (too thin) on the touchscreen, the user can zoom-in on a region of the lumen contour to increase the size of the image to have a better view of at least part of the lumen contour 400. For example, in one embodiment, the touch sensing range 425 for touching the lumen contour 40o has a width of around 20 pixels on the touchscreen. In this case, when the user touches a spot along the lumen contour 400, the computer recognizes the touched region of the screen, and will first try to identify the closest control point within the touch sensing range 425. If the computer finds a control point within the touch sensing range 425 (e.g., within 20 pixels), the computer highlights or otherwise marks the control point as active. Otherwise, the computer will automatically add a control point to the spot touched by the user on the lumen contour 40o within the touch sensing range 425.

In some embodiments it may not be advisable for the user to add the control points by clicking on the curve of the lumen contour due to accuracy concerns; but adding control points can be an optional function of the editing tool. Moreover, as shown in FIG. 3, the user is given an option to choose the number of control points to be added. To improve accuracy, the user can take advantage of the concept of anchor points. As explained above, instead of adding control points by clicking or touching on the curve of the lumen contour 400, the user can set anchor points by drawing lines from outside of the contour to the inside of the contour, and the intersection between the drawn lines and the segment of the lumen contour defines an anchor point as shown in FIG. 7.
<Display and Use Virtual TouchPad>

The use of a Virtual TouchPad is similar to the conventional TouchPad used in laptop computers and similar devices. A conventional TouchPad gives a separate area for the finger of user to touch and move a pointing arrow around the screen of a display. Notably, in contrast to a conventional TouchPad that is fixed to a portion of the keyboard, in the present disclosure, a Virtual Touchpad is synchronized with a start point (or any point being edited) on the touchscreen. In this manner, when the user touches a point on the touchscreen, and draws a line across or over the lumen contour 400, the corresponding path being drawn can be observed on the same screen in a magnified view on the original location of the screen. Since the system can take advantage of the touchscreen functionality of display device 250, it is possible to dynamically display the Touchpad area as a window on the touchscreen. We name this feature a Virtual Touchpad.

An enhancement for the Virtual Touchpad is to configure the system to display the underlying tomographic image 321, and draw the lumen contour on the Virtual Touchpad defined region (e.g., a window on GUI 300). During the editing process, the Virtual Touchpad can display images in different scale factors, such as with a zoom factor (e.g., ×1.2, ×2.5, ×5, ×10) so that the user can have better details for image assessment. Given the high resolution of modern medical displays, the Virtual Touchpad can have a limited size and still offer sufficient information to the user even when zoomed to its maximum zooming capacity. In some embodiments, the Virtual Touchpad can slide along with the movement of the user's finger and keep the touch location at the approximate center of the dynamically displayed window. This will greatly increase the active region of the Touchpad relative to the original tomographic image.

A workflow (process steps) for controlling the editing process while using the Virtual Touchpad feature can be summarized as follows:

Touch the touch screen with finger to engage the start point on screen and the point on touch pad.

In the contour editing mode, a long press on a point on the touchscreen will define a starting point. For editing mode A, this press needs to be either on a control point 402, or on the curve of contour 400 with a control point 402 being automatically added to the contour 400. Then the subsequent move of this control point will drag the contour segment. For editing mode B, this press can be on an anchor point (also for mode C), or any point outside the contour's active region. Then the start point is either the anchor point or a free point, the subsequent move will draw a curved line over the underlying OCT image. To define the second point as the starting point on the virtual touch pad, it is possible to use two different approaches, which will be described next in detail. After the initial step, there are two points associated with the same spot on the underlying image, but displayed the same region of interests at different locations.

A next step is to adjust the zoom factor on the virtual touchpad before drawing the desired curve. This step is optional. By default, the system can set a zoom factor like ×1.2 or ×2.0 to give user a better view of details in the underlying tomographic image on the touchpad region. The user can adjust the zoom factor by a zoom gesture (e.g., pinching with two fingers to select a portion of the image and expanding the two fingers away from each other). Alternatively, zooming can be accomplished by either virtual or mechanical slide-bar tools.

Draw the curve using touch pad area and watch the monitor the feedback results on both regions. Once the drawing is complete, lifting the finger point off the screen terminates the drawing operation. The results are displayed the same way as it was displayed during the process. The curve being drawn by the user is usually distinguished from the original curve using a different color. For example, the original contour curve is in orange, while the new curve drawn is in green or blue.

After a drawing step is done, the auto-smooth corner point process will be triggered automatically to improve the intersection corner and display the final smoothed curve shape with the color of the contour being the original color. The Virtual Touchpad improves the curve drawing accuracy by providing non-blocked view and zoomed view on the Virtual Touchpad region. The feature is illustrated in FIG. 10.

<Virtual Touchpad with Multi-Touch Feature>

In some embodiments, to engage the start point on the touchscreen and the point on a touch pad, if the touchscreen and multi-touch feature is available, the point synchronization initialization process utilizes special gestures using two fingers. Starting with the index finger to select and hold the start point, the second finger, for example, the thumb will touch the screen at a different location on the touchscreen. The new location is used as the start point on the virtual touch pad, and a window will be displayed around the start point with the contour curve and underlying image matching the original start point selected. The virtual touch pad window is now following the position (movement) of the second finger, and the system ensures the first position is now fixed. Then the user can lift the first index finger from the touchscreen and the virtual touchpad window will stay unchanged. However, because the user will generally like to use the index finger instead of the thumb to draw curves, the user can find a new desired place, and place the index finger on the touchscreen again, then lift the thumb. During this process, the virtual touchpad window jumps to new place as the index finger is pointing to and the original start point location is still marked and not moved at all. This kind of two finger-walking steps can go on multiple times for the user to reach the ideal location and comfort before completing the editing process. It is worth mentioning that, because small movements can happen at the fingertip in touch, the virtual touchpad is generally following the latest movements of the finger, and the original start point remains unchanged during such process. This is called the virtual Touchpad initialization stage. Finally, in order to fix the targeted drawing window, we employ a new gesture to use two of more fingers to tap on the touchscreen, sending a multi-touch signal to indicate that the user is ready to draw using the remaining (likely the index) finger on the screen.

<Virtual Touchpad Combined with Pointing Device>

In some embodiments, to ensure back compatibility for a system without a multi-touch capability, there is a different way to engage the start point on screen and the point on touchpad just by using a regular mouse. In this case, the user can press and hold on to the starting point with a long press (for example: from 1 to 3 seconds), then the virtual touchpad will automatically show up at a corner of the screen to introduce least impacts to the working area. Then user can release the mouse, and the virtual touchpad and the select points on both original window and the new window will still be present. Then user can move the mouse to select the point on the virtual touchpad, press it down and continue to move to draw the desired curve. Because the virtual touchpad is a floating window on top of original window, before the drawing activity, the user can adjust the touchpad by moving it to a desired location and changing the zoom factor. Moreover, the rest of the drawing activities will be the same as the multi-touch supported mode when initialization is done and the virtual touchpad is fixed.

<Overall Process of the Edit Tool>

In a process applied to modify the lumen contour 400 resulted from algorithmic lumen detection, the system starts with a contour shape, and compares the lumen contour with the underlying image. The system or the user decides if automatically-generated lumen contour needs to be edited.

The system enters the contour editing mode by receiving input from the user that touches, presses, or otherwise activates the edit mode button.

If the contour 400 does not match with underlying image at all, the user can use the system to clear the contour 400, and use Mode C to redraw the contour.

If the contour 400 has a large portion matching the true lumen edge of tomographic image, but there is a substantial portion not matching, the user can use Mode B to directly draw one or more lines that intersects with the contour to cut-off a segment of the contour having the difference region, and to redraw the portion the contour.

If the contour has a large portion matching the true lumen edge of the image, and there is a portion of the contour with a difference that is not very large, the user can set two anchor points, and then use editing Mode A to drag the segment with the limited range to desired place.

If the contour has a segment mismatching the image, but very close to the smoothed shape, the user can set and select two anchor points, and then use Mode C to click on the edges on the underlying image and interpolate the segment accordingly.

User can add, change or delete control points and anchor points when needed, given a certain minimum distance limit between any two neighboring points. Using double-click on the control and anchor points to toggle their types when needed.

User can use undo/redo to compare intermediate results in between and keep the better ones using key bookmarks.

After each modification is complete, user can repeat the steps above (go to step 3) for any additional contour changes necessary.

Finally, when user is satisfied with the contour results, the user can touch the edit mode button to quit the edit mode and all control and anchor points will be removed. FIG. 3 presents the flowchart of combining all editing modes together when making contour changes.

<Feedback View to Improve Efficiency of Editing Tool>

Intuitive actions and feedback view make the tool easy to learn. In any of the editing mode mentioned above, there are contour curve changes displayed on the screen in response to user's movements. The feedbacks help the user to evaluate if the desired results have been reached. In some cases, a single move will finish a contour editing change. If the result is not desirable, user can simply click the "Undo" button to recover the previous stage. In other cases, the contour editing change may need multiple steps. During the process, user may choose to cancel the editing at any time by clicking the "Esc" button. Once the change is complete, the whole thing can be discarded by the "Undo" button, then bring back by "Redo" button. In addition, the intermediate steps are generally not preserved for modification.

Below is described an example of a contour editing process, which demonstrates the intuitive steps that a user can take to achieve the desired contour shape changes. The description is not a chronological list of one-directional process steps. Rather, the editing process is an iterative process which allows the user to interactively operate the system observe the editing results in real time. During each step as well as the end of each operation, the user can see through the feedback results and may adjustments accordingly.

Assumptions: 1. The closed curve of the automatically generated lumen contour 400 is already displayed on the screen (e.g., as shown in FIG. 2A at section 320). 2. The objective is to edit the curve of lumen contour 400 into a different one so that the computer generated lumen contour appropriately matches the true lumen edge 322 of the tomographic image 321.

General usage steps and scenarios—exemplary action sequence:

1. Enter Edit Mode: Activate/operate Edit Mode button.
2. Extra Hints: 2a) shows a narrow touch sensing range (shadow band) that limits the response around the contour curve, a touch anywhere inside the touch sensing range will be equivalent to a mouse click on the contour curve, and the system will auto find the closest control point on the curve of contour 400. 2b) the system can add a hint button or a popup window (bubble) for displaying simple instruction to the user on valid operations (e.g., "touch within shadow band to edit").
3. Adding Control Points: 3a) use button 508—add N control points evenly distributed around lumen contour 400; 3b) touch on curve/shadow band to add control points one by one; 3c) freehand draw from outside to inside to intersect the contour curve—add an anchor point; 3d) touch on control point to select; 3e) long press (optionally double click) on control point to change type from control point to anchor point and vice versa; 3f) Draw from inside to outside to delete undesired control point and/or anchor point.
4. Drag and move actions depend on the locations: 4a) on the curve, add a control point; 4b) on curve's control point, move and interpolate the segment defined by neighboring control points; 4c) anchor point, draw from one anchor point to another anchor point; 4d) inside/outside curve, draw a curve and intersect with contour, when both start and end points are on the same side; otherwise, test if intersection is valid to add an anchor point.
5. Press down before move, apply two finger gesture to trigger multi-touch, and to show virtual touchpad window; adjust starting point on touchpad window with starting point fixed. 5a) leave two finger gesture and apply it again will move the touchpad window location; 5b) without leaving two finger gesture and go back to press down state long enough, drawing action cannot be enabled and the touchpad will be canceled.
6. Drag and Move fast from a starting point will begin to draw the curve. 6a) If a control point is selected, apply Mode A, drag and interpolate the segment; 6b) If an anchor point is selected, apply Mode B, drag and draw the segment to target anchor point; 6c) If either an insider or outside point is selected, still apply Mode B, drag and draw the segment to intersect with existing contour.
7. If an anchor point is selected, apply three finger gesture before dragging, Mode C will be used to interpolate between two anchor points. 7a) touch or click on the lumen edge will add a control point and interpolation happens between two anchor points; 7b) touch or click on the target anchor point will complete the contour editing using mode C; otherwise, the entire editing results will be discarded as incomplete.
8. Use Clear Contour button will discard the whole contour curve, Mode C will be used in such condition. 8a) touch or click on the lumen edge will add a control point and interpolation happens among all control points to form a contour after the number of control points is larger than 2. 8b) touch or click on the first control point will complete the editing using mode C;

otherwise, if the contour is intersecting itself, the entire editing results will be discarded as incomplete and the contour needs to be manually redrawn.

9. After complete of one type of editing, auto-interpolation is conducted to smooth the editing results: 9a) user can choose Undo/Redo action to select the desired results. 9b) user can modify the control points and anchor points by returning to step 3 for next round of editing. 9c) user can exit the editing mode: use "complete" button/step.

10. Exit Edit Mode. Touch or Click the EditMode button.

11. Extra buttons to assists the editing feature. As described above, Buttons A to D can be used a group buttons for predetermined settings of the user interface. Alternatively, buttons A to D can be dedicated buttons with alternative functions, as follows:

Button A: Edit Mode button, touch or click button A to enter and end the edit mode at any time;

Button B, Virtual TouchPad feature button, touch or click button B to enable or disable the Virtual Touchpad feature;

Button C, Show/clear control points. Touch or click button C to clear all existing control, anchor points and evenly distribute control points around the contour. Can be a combo box with a pulldown menu for the user to choose a number. For example, the user can choose 2, 4, 6, 8 and up to 16 or more points. The system can be programmed to place the chosen number of control points as close as possible to the true lumen edge 322 of the tomographic image 321 to replace a deleted segment of the computer-generated lumen contour 400;

Button D: Allows the user to interactively input Undo and Redo instructions to evaluate the editing results. Any button may be auto greyed out if not applicable during a given operation. See FIG. 3 for buttons used for editing mode.

12. Double tap or double click operations: 12a) double tap or double click on a control or anchor point, causes the type of point to change but the curve does not change (remains in its current location); 12b) given two anchor points, double tapping or double clicking the curve in between will smooth the curve between two anchor points by executing a spline interpolation (e.g., a cubic spline interpolation).

The foregoing embodiments provide an intuitive, flexible, easy to use contour editing tool, which combines multiple contour manipulation modes. A user can make desired contour shape changes with fewer steps using different modes together on the same user interface. The editing tool offers touchscreen capability, and mouse free configuration. Regular mouse input compatibility is optionally available. The contour editing tool with touchscreen capability enables multiple editing options to coexist under a single interface. The contour editing tool includes an intelligent algorithm that provides automated feedback to the user through the editing process to achieve the best results in a short time. All the effective editing actions are cached for "Undo" and "Redo" actions so that user can learn editing features quickly, and gain confidence by using them repetitively back-and-forth, without worries about losing the desired results when making any mistakes.

Other Embodiments and Modifications

All of the foregoing embodiments can be modified and/or combined with each other to provide one or more of the following features and advantages.

The use of control points for defining a lumen contour is known. The present application improves on the use of control points by making control points draggable by a touchscreen interface, according to an amount of editing which is determined based on one or more thresholds (e.g., according to editing modes A, B, or C). The present application also improves by converting control points into anchor points for selective contour curve manipulation of one or more segments. This allows the user to have clear control of the region-of-interest (ROI) affected by the adjustment.

Use multi-touchscreen gestures and touch limiting band (touch sensing range) to improve input accuracy. This includes using slice drawing across a contour to create anchor points, and using a virtual touchpad for zooming or panning to avoid view blocking and improve editing accuracy.

For an anchor point, the intersection point between a drawn line and the contour is more accurate and better defined as an anchor point. When an existing anchor point is not at the desired location, the user can draw a perpendicular line across the arc of the contour from outside to inside (or from inside to outside), the point of intersection between the drawn line and the arc of the contour is the new anchor point. If the previously existing anchor point and the new anchor point are too close, the user can replace either of the points by repeating the process.

One embodiment introduces a virtual touchpad for synchronized dragging and drawing. The virtual touchpad allows the user's finger to move to a different location from the actually curve displayed to avoid visual blocking. Supports drag sensitivity changing using a virtual touch pad with different zoom factor and multi-touch gestures.

The system allows easily add/delete control points by single tap or click and double tap or double click within touch sensing range for receiving user input actions. Displays a shadow band indicative of touch sensing range where the user can touch the lumen contour for easy user interaction. Shadow band or touch sensing range indicates the range where the user can touch for accurate editing. Here, the shadow band has visible display effects, and is associated with movement of the user's finger or movement of an existing input mechanism (e.g., a mouse). When the control point is in dragging mode, the shadow band displayed around the original curve of the computer generated contour 400 will be fixed to the curve shape before the dragging mode is entered, and the control point movement will be stopped when the finger or mouse position is out of the shadow band. In other words, the touch sensing range 425 is associated with a movement of a fingertip acting on the touchscreen to move a control point such that, when a control point is dragged by the fingertip of a user touching the lumen contour and the shadow band, the lumen contour and shadow band move together with the control point, and control point movement is stopped when the fingertip is out of the shadow band. Only when the user's finger or the mouse pointer moves to reenter the shadow band (preferably at the same location where it exited), will the dragging movement resume for a given control point. In this manner, the shadow band serves as touch sensing range that provides a hint for the user to limit the dragging of the control point; this helps in avoiding unintended or excessive changes to the contour that can result in undesirably removing parts of the contour.

Notably, as described throughout, the system seemingly mixes multiple editing modes (3 or more) to change the contour shape for different cases with the same editing tool.

The system ensures that the minimum distance between points are applied and desired changes are displayed instantly as feedback to user. Allows undo/redo and preserved previous results for the user to choose the best editing results.

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by persons of ordinary skill in the art to which this disclosure belongs. In that regard, breadth and scope of the present disclosure is not limited by the specification or drawings, but rather only by the plain meaning of the claim terms employed.

In describing exemplary embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A method comprising:
providing a tubular sheath that is flexible and defines a first lumen which extends from a proximal end to a distal end of the tubular sheath;
receiving, by a processor, image data corresponding to a plurality of tomographic images acquired by an imaging catheter scanning a blood vessel;
obtaining, by the processor, an automatically-generated lumen contour of the blood vessel from a tomographic image of the blood vessel;
displaying, on a display, the automatically-generated lumen contour overlaid on the tomographic image of the blood vessel;
identifying a true lumen edge of the blood vessel in the tomographic image;
estimating, by the processor, a percentage of matching between a shape of the automatically-generated lumen contour to a shape of the true lumen edge; and
receiving editing operations from a user via a touchscreen interface for editing at least part of the automatically-generated lumen contour based on the estimated percentage of matching,
wherein, in a case where the estimated percentage of matching is equal to or greater than 80%, the editing operations include:
adding at least one control point on at least part of the automatically-generated lumen contour, and
dragging the at least one control point together with the at least part of the automatically-generated lumen contour so that the at least part of the automatically-generated lumen contour matches a corresponding part of the true lumen edge of the blood vessel within the tomographic image.

2. The method according to claim 1,
wherein estimating the percentage of matching is a metric defined by using a full circle of the automatically-generated lumen contour as the 100%,
comparing a predetermined number of evenly distributed sample points of the full circle of the automatically-generated lumen contour to a correspondingly evenly distributed and equal number of sample points of the true lumen edge, and
determining the percentage of the sample points of the automatically-generated lumen contour that match the sample points of the true lumen edge.

3. The method according to claim 1,
wherein dragging the at least one control point includes moving the at least one control point towards or away from a center of the tomographic image the percentage of matching becomes as close as possible to 100%.

4. The method according to claim 1,
wherein, in a case where the estimated percentage of matching is less than 80% and equal to or greater than 60%, the editing operations include:
deleting a segment of the automatically-generated lumen contour that does not match the true lumen edge; and
replacing the deleted segment to obtain an edited lumen contour.

5. The method according to claim 4,
wherein deleting includes cutting a segment of the automatically-generated lumen contour in two locations corresponding to a start and end of the portion of the automatically-generated lumen contour that does not match the true lumen edge,
wherein replacing includes adding an anchor point on each of the start and end locations, adding at least one control point on the new contour segment between the two anchor points and connecting the control point with two anchor points to form an edited lumen contour.

6. The method according to claim 5, further comprising:
moving the control point along with the new contour segment until the edited lumen contour has a percentage of matching equal to or greater than 80%.

7. The method according to claim 1,
wherein, in a case where the estimated percentage of matching is less than 60% and equal to or greater than 25%, the editing operations include:
removing the automatically-generated lumen contour,
adding a plurality of control points along the true lumen edge of the blood vessel within the tomographic image, and
connecting the plurality of control points along the lumen edge of the blood vessel to generate a new lumen contour.

8. The method according to claim 7, further comprising:
adding one or more anchor points along the new lumen contour; and
dragging one or more of the control points together with portions of the new lumen contour until the matching percentage between the new lumen contour and the true lumen edge becomes equal to or greater than 80%.

9. The method according to claim 1,
wherein estimating the percentage of matching includes comparing the shape of the automatically-generated lumen contour to the shape of the true lumen edge, and determining whether the percentage of matching meets one or more of a plurality of thresholds.

10. The method according to claim 9,
wherein the editing operations include one or more of:
in a case where the estimated percentage of matching is
equal to or less than a lowest threshold, completely
removing the automatically-generated lumen contour,
and
drawing a new lumen contour by adding a plurality of
control points along the true lumen edge of the blood
vessel in the tomographic image, and connecting the
plurality of control points along the lumen edge of the
blood vessel to generate a new lumen contour,
in a case where the estimated percentage of matching is
equal to or greater than a highest threshold, adding at
least one control point on at least part of the automati-
cally-generated lumen contour, and dragging the at
least one control point together with the at least part of
the automatically-generated lumen contour so that the
at least part of the automatically-generated lumen con-
tour matches a corresponding part of the true lumen
edge of the blood vessel in the tomographic image, and
in a case where the estimated percentage of matching is
greater than the lowest threshold and lower than the
highest threshold, deleting a segment of the automati-
cally-generated lumen contour that does not match the
true lumen edge, and replacing the deleted segment
with a with a manually drawn segment of lumen
contour.

11. The method according to claim 1,
wherein the tactile interface is a touchscreen interface
provided on the display device,
wherein adding at least one control point includes the
user:
touching with a fingertip on at least part of the automati-
cally-generated lumen contour for a predetermined
amount of time, and the processor adding a new control
point or selecting an existing control point, and
dragging the at least one control point together with the at
least part of the automatically-generated lumen contour
includes the user moving the fingertip in a direction
towards or away from a center of the tomographic
image so that the at least part of the automatically-
generated lumen contour matches a corresponding part
of the true lumen edge of the blood vessel.

12. The method according to claim 4,
wherein the tactile interface is a touchscreen interface
provided in the display device,
wherein replacing the segment of the automatically-gen-
erated lumen contour includes the user touching with a
fingertip the touchscreen interface and moving the
fingertip to draw a line that intersects a segment of the
automatically-generated lumen contour in two loca-
tions corresponding to a start and end of the portion of
the automatically-generated lumen contour that does
not match the true lumen edge.

13. The method according to claim 12, further compris-
ing:
automatically adding an anchor point on each of the start
and end locations,
connecting the two anchor points to generate a new
contour segment, and
adding at least one new control point on the new contour
segment between the two anchor points.

14. The method according to claim 13, further compris-
ing:
the user touching with the fingertip the touchscreen inter-
face and moving the fingertip to drag the at least one
new control point along with the new contour segment
until the edited lumen contour has a percentage of
matching equal to or greater than 80%.

15. A non-transitory storage medium storing thereof com-
puter-executable instructions, which when executed by a
processor, cause the processor to implement the method
according to claim 1.

16. A system comprising:
a processor configured to:
receive image data corresponding to a plurality of tomo-
graphic images acquired by an imaging catheter scan-
ning a blood vessel;
obtain an automatically-generated lumen contour of the
blood vessel from a tomographic image of the blood
vessel;
display, on a display device, the automatically-generated
lumen contour overlaid on the tomographic image of
the blood vessel;
identify a true lumen edge of the blood vessel in the
tomographic image;
estimate a percentage of matching between a shape of the
automatically-generated lumen contour to a shape of
the true lumen edge; and
receive editing operations from a user via a touchscreen
interface for editing at least part of the automatically-
generated lumen contour based on the estimated per-
centage of matching,
wherein, in a case where the estimated percentage of
matching is equal to or greater than 80%, the editing
operations include:
adding at least one control point on at least part of the
automatically-generated lumen contour, and
dragging the at least one control point together with the at
least part of the automatically-generated lumen contour
so that the at least part of the automatically-generated
lumen contour matches a corresponding part of the true
lumen edge of the blood vessel within the tomographic
image.

17. The system according to claim 16,
wherein the processor estimates the percentage of match-
ing by comparing the shape of the automatically-
generated lumen contour to the shape of the true lumen
edge, and determines whether the percentage of match-
ing meets one or more of a plurality of thresholds
including at least a lowest threshold and a highest
threshold.

18. The system according to claim 17,
wherein the editing operations for editing include one or
more of:
in a case where the estimated percentage of matching is
equal to or less than the lowest threshold, the process
receives operations for completely removing the auto-
matically-generated lumen contour, and drawing a new
lumen contour by adding a plurality of control points
along the true lumen edge of the blood vessel in the
tomographic image, and connecting the plurality of
control points along the lumen edge of the blood vessel
to generate a new lumen contour,
in a case where the estimated percentage of matching is
equal to or greater than a highest threshold, the pro-
cessor receives operations for adding at least one
control point on at least part of the automatically-
generated lumen contour, and dragging the at least one
control point together with the at least part of the
automatically-generated lumen contour so that the at
least part of the automatically-generated lumen contour
matches a corresponding part of the true lumen edge of
the blood vessel in the tomographic image, and in a case where the estimated percentage of matching is greater than the lowest threshold and lower than the highest threshold, the processor receives operations for deleting a segment of the automatically-generated lumen contour that does not match the true lumen edge, and replacing the deleted segment with a with a manually drawn segment of lumen contour.

19. The system according to claim 16, wherein the touchscreen interface is configured to display the automatically-generated lumen contour overlaid onto to a touch sensing range displayed as a shadow band.

20. The system according to claim 19, wherein, when the user touches a spot along the lumen contour, the processor is configured to detect the touched region of the touchscreen, and to search a control point nearest to the touched region within the touch sensing range.

21. The system according to claim 20, wherein, in a case where the processor identifies a control point within the touch sensing range, the process marks the control point as active, and wherein, in a case where the processor does not identify a control point within the touch sensing range, the processor is configured to automatically add a control point to lumen contour on the spot touched by the user within the touch sensing range.

22. The system according to claim 19, wherein the touch sensing range is associated with a movement of a fingertip acting on the touchscreen such that when a control point is dragged by the fingertip of a user touching the lumen contour and the shadow band, the lumen contour and shadow band move together with the control point, and control point movement is stopped when the fingertip is out of the shadow band.

* * * * *